US008925164B2

(12) United States Patent
Vesely

(10) Patent No.: US 8,925,164 B2
(45) Date of Patent: Jan. 6, 2015

(54) VALVE ASSEMBLY WITH EXCHANGEABLE VALVE MEMBER AND A TOOL SET FOR EXCHANGING THE VALVE MEMBER

(75) Inventor: Ivan Vesely, Larkspur, CO (US)

(73) Assignee: ValveXchange Inc., Aurora, CO (US)

( * ) Notice: Subject to any disclaimer, the term of this patent is extended or adjusted under 35 U.S.C. 154(b) by 615 days.

(21) Appl. No.: 13/063,218

(22) PCT Filed: Sep. 11, 2009

(86) PCT No.: PCT/US2009/056633
§ 371 (c)(1),
(2), (4) Date: Mar. 10, 2011

(87) PCT Pub. No.: WO2010/030859
PCT Pub. Date: Mar. 18, 2010

(65) Prior Publication Data
US 2011/0167603 A1   Jul. 14, 2011

Related U.S. Application Data

(60) Provisional application No. 61/096,540, filed on Sep. 12, 2008.

(51) Int. Cl.
*B23P 19/04* (2006.01)
*A61F 2/24* (2006.01)
*A61F 11/00* (2006.01)
*A61F 2/95* (2013.01)

(52) U.S. Cl.
CPC ............ *A61F 2/2427* (2013.01); *A61F 2/2412* (2013.01); *A61F 2002/9528* (2013.01); *A61F 2250/006* (2013.01); *A61F 2/2409* (2013.01)
USPC .......................... 29/221.6; 623/2.11; 606/108

(58) Field of Classification Search
USPC ............ 29/213.1, 221.6, 214, 220, 249, 268, 29/255, 278; 269/32, 24, 228; 623/2.1, 623/2.11; 606/108, 205–211
See application file for complete search history.

(56) References Cited

U.S. PATENT DOCUMENTS 3,409,013 A   11/1968 Berry ................................. 606/1
3,839,741 A   10/1974 Haller .......................... 623/2.34
(Continued)

FOREIGN PATENT DOCUMENTS

WO   WO 96/14032   5/1996   ................ A61F 2/24
WO   WO 99/33414   7/1999   ................ A61F 2/24
(Continued)

OTHER PUBLICATIONS

European Search Report for European Patent Application No. 01 98 7412.2, Oct. 19, 2006.
(Continued)

*Primary Examiner* — Lee D Wilson
*Assistant Examiner* — Nirvana Deonauth
(74) *Attorney, Agent, or Firm* — Kusner & Jaffe

(57) ABSTRACT

A valve assembly with an exchangeable valve member and a docking station, and a tool set that facilitates the exchange of a valve member. The tool set includes a stabilizer or holding tool for holding the docking station during an exchange procedure, a valve extraction or removal tool for removing an existing valve member from an installed docking station, and an insertion tool for installing a replacement valve member.

12 Claims, 22 Drawing Sheets

(56) References Cited

U.S. PATENT DOCUMENTS

| | | | | |
|---|---|---|---|---|
| 3,872,760 A * | 3/1975 | Desnoyers, Jr. | | 83/743 |
| 3,898,701 A | 8/1975 | LaRussa | | 3/1.5 |
| 4,056,854 A | 11/1977 | Boretos et al. | | 3/1.5 |
| 4,501,030 A | 2/1985 | Lane | | 3/1.5 |
| 4,506,394 A | 3/1985 | Bédard | | 3/1.5 |
| 4,535,483 A | 8/1985 | Kiawitter et al. | | 623/2.4 |
| 4,680,031 A | 7/1987 | Alonso | | 128/343 |
| 4,687,483 A | 8/1987 | Fisher et al. | | 623/2.14 |
| 4,705,516 A | 11/1987 | Barone et al. | | 623/2.39 |
| 4,733,665 A | 3/1988 | Palmaz | | 604/107 |
| 4,790,843 A | 12/1988 | Carpentier et al. | | 623/2 |
| 4,887,605 A | 12/1989 | Angelsen et al. | | 128/660.03 |
| 4,909,789 A | 3/1990 | Taguchi et al. | | 604/107 |
| 4,917,698 A | 4/1990 | Carpentier et al. | | 623/2 |
| 5,037,427 A | 8/1991 | Harada et al. | | 606/108 |
| 5,041,130 A | 8/1991 | Cosgrove et al. | | 623/2 |
| 5,061,275 A | 10/1991 | Wallsten et al. | | 623/1 |
| 5,071,431 A | 12/1991 | Sauter et al. | | 623/2 |
| 5,087,264 A | 2/1992 | Miller et al. | | 606/159 |
| 5,113,846 A | 5/1992 | Hiltebrandt et al. | | 600/225 |
| 5,163,953 A | 11/1992 | Vince | | 623/2 |
| 5,197,978 A | 3/1993 | Hess | | 623/1.18 |
| 5,234,443 A | 8/1993 | Phan et al. | | 606/148 |
| 5,312,360 A | 5/1994 | Behl | | 604/164 |
| 5,336,230 A | 8/1994 | Leichtling et al. | | 606/148 |
| 5,411,552 A | 5/1995 | Andersen et al. | | 623/2 |
| 5,474,563 A | 12/1995 | Myler et al. | | 606/194 |
| 5,476,510 A | 12/1995 | Eberhardt et al. | | 623/2.11 |
| 5,545,214 A | 8/1996 | Stevens | | 623/2 |
| 5,549,665 A | 8/1996 | Vesely et al. | | 623/2 |
| 5,554,185 A | 9/1996 | Block et al. | | 623/2 |
| 5,571,174 A | 11/1996 | Love et al. | | 623/2 |
| 5,584,803 A | 12/1996 | Stevens et al. | | 604/4 |
| 5,593,424 A | 1/1997 | Northrup III | | 606/232 |
| 5,607,446 A | 3/1997 | Beehler et al. | | 606/198 |
| 5,662,676 A | 9/1997 | Koninckx | | 606/198 |
| 5,667,525 A | 9/1997 | Ishibashi | | 606/206 |
| 5,718,725 A | 2/1998 | Sterman et al. | | 623/2 |
| 5,755,783 A | 5/1998 | Stobie et al. | | 623/2 |
| 5,807,405 A | 9/1998 | Vanney et al. | | 623/112 |
| 5,814,054 A | 9/1998 | Kortenbach et al. | | 606/139 |
| 5,840,081 A | 11/1998 | Andersen et al. | | 623/1.11 |
| 5,843,103 A | 12/1998 | Wulfman | | 606/159 |
| 5,843,181 A | 12/1998 | Jaffe et al. | | 623/2 |
| 5,855,601 A | 1/1999 | Bessler et al. | | 623/2 |
| 5,910,144 A | 6/1999 | Hayashi | | 606/108 |
| 5,910,170 A | 6/1999 | Reimink et al. | | 623/2 |
| 5,928,281 A | 7/1999 | Huynh et al. | | 623/2 |
| 5,957,949 A | 9/1999 | Leonhardt et al. | | 606/194 |
| 5,961,545 A | 10/1999 | Lentz et al. | | 623/1 |
| 5,968,070 A | 10/1999 | Bley et al. | | 606/198 |
| 6,004,328 A | 12/1999 | Solar | | 606/108 |
| 6,071,263 A | 6/2000 | Kirkman | | 604/104 |
| 6,074,418 A | 6/2000 | Buchanan et al. | | 623/2.11 |
| 6,106,550 A | 8/2000 | Magovern et al. | | 623/2.38 |
| 6,143,025 A | 11/2000 | Stobie et al. | | 623/2.39 |
| 6,156,055 A | 12/2000 | Ravenscroft | | 606/206 |
| 6,168,614 B1 | 1/2001 | Andersen et al. | | 623/1 |
| 6,168,616 B1 | 1/2001 | Brown | | 623/1.11 |
| 6,187,016 B1 | 2/2001 | Hedges et al. | | 606/108 |
| 6,197,054 B1 | 3/2001 | Hamblin, Jr. et al. | | 623/2.38 |
| 6,217,585 B1 | 4/2001 | Houser et al. | | 606/108 |
| 6,249,952 B1 | 6/2001 | Ding | | 29/460 |
| 6,299,638 B1 | 10/2001 | Sauter | | 623/1.26 |
| 6,312,465 B1 | 11/2001 | Griffin et al. | | 623/2.38 |
| 6,371,983 B1 | 4/2002 | Lane | | 623/2.14 |
| 6,383,205 B1 | 5/2002 | Samson et al. | | 606/200 |
| 6,454,799 B1 | 9/2002 | Schreck | | 623/2.18 |
| 6,461,382 B1 | 10/2002 | Cao | | 623/2.19 |
| 6,508,827 B1 | 1/2003 | Manhes | | 606/205 |
| 6,530,952 B2 | 3/2003 | Vesely | | 623/2.18 |
| 6,562,065 B1 | 5/2003 | Shanley | | 623/1.15 |
| 6,569,196 B1 | 5/2003 | Vesely | | 623/2.14 |
| 6,579,305 B1 | 6/2003 | Lashinski | | 623/1.11 |
| 6,629,534 B1 | 10/2003 | St. Goar et al. | | 128/898 |
| 6,663,664 B1 | 12/2003 | Pacetti | | 623/1.2 |
| 6,733,525 B2 | 5/2004 | Yang et al. | | 623/2.17 |
| 6,769,434 B2 | 8/2004 | Liddicoat et al. | | 128/898 |
| 6,821,297 B2 | 11/2004 | Snyders | | 623/2.18 |
| 6,893,459 B1 * | 5/2005 | Macoviak | | 623/2.11 |
| 7,011,681 B2 | 3/2006 | Vesely | | 623/211 |
| 7,041,132 B2 | 5/2006 | Quijano et al. | | 623/2.11 |
| 7,063,707 B2 | 6/2006 | Bose et al. | | 606/127 |
| 7,105,009 B2 * | 9/2006 | Johnson et al. | | 606/205 |
| 7,201,761 B2 | 4/2007 | Woolfson et al. | | 606/170 |
| 7,235,093 B2 | 6/2007 | Gregorich | | 623/1.11 |
| 7,323,003 B2 | 1/2008 | Lowe | | 606/200 |
| 7,329,279 B2 | 2/2008 | Haug et al. | | 623/2.11 |
| RE40,377 E | 6/2008 | Williamson et al. | | 623/2.11 |
| 7,381,219 B2 | 6/2008 | Salahieh et al. | | 623/2.11 |
| 7,544,206 B2 | 6/2009 | Cohn | | 623/2.11 |
| 7,815,676 B2 | 10/2010 | Greenberg | | 623/2.11 |
| 7,824,442 B2 | 11/2010 | Salahieh et al. | | 623/2.11 |
| 7,824,443 B2 | 11/2010 | Salahieh et al. | | 623/2.11 |
| 7,959,666 B2 | 6/2011 | Salahieh et al. | | 623/1.26 |
| 7,959,672 B2 | 6/2011 | Salahieh et al. | | 623/2.17 |
| 7,993,362 B2 | 8/2011 | Lowe et al. | | 606/200 |
| 8,025,668 B2 | 9/2011 | McCartney | | 606/106 |
| 2001/0002445 A1 | 5/2001 | Vesely | | 623/2.11 |
| 2002/0055775 A1 | 5/2002 | Carpentier et al. | | 623/2.17 |
| 2002/0128702 A1 | 9/2002 | Menz et al. | | 623/1.12 |
| 2002/0173811 A1 | 11/2002 | Tu et al. | | 606/159 |
| 2002/0198594 A1 | 12/2002 | Schreck | | 623/2.11 |
| 2003/0055495 A1 | 3/2003 | Pease et al. | | 623/2.11 |
| 2003/0125793 A1 | 7/2003 | Vesely | | 623/1.11 |
| 2004/0015232 A1 | 1/2004 | Shu et al. | | 623/2.4 |
| 2004/0030381 A1 | 2/2004 | Shu | | 623/2.11 |
| 2004/0039442 A1 | 2/2004 | St. Goar et al. | | 623/2.36 |
| 2004/0147939 A1 | 7/2004 | Rabkin et al. | | 606/108 |
| 2004/0186563 A1 | 9/2004 | Lobbi | | 623/2.11 |
| 2004/0186565 A1 | 9/2004 | Schreck | | 623/2.18 |
| 2004/0225356 A1 | 11/2004 | Frater | | 623/2.14 |
| 2005/0075717 A1 | 4/2005 | Nguyen et al. | | 623/1.26 |
| 2005/0137692 A1 | 6/2005 | Haug et al. | | 623/2.11 |
| 2005/0159811 A1 | 7/2005 | Lane | | 623/2.14 |
| 2005/0165479 A1 | 7/2005 | Drews et al. | | 623/2.38 |
| 2005/0203614 A1 | 9/2005 | Forster et al. | | 623/2.11 |
| 2005/0203618 A1 | 9/2005 | Sharkawy et al. | | 623/2.38 |
| 2005/0216079 A1 | 9/2005 | MaCoviak | | 623/2.38 |
| 2005/0228494 A1 | 10/2005 | Marquez | | 623/2.18 |
| 2005/0228495 A1 | 10/2005 | Macoviak | | 623/2.18 |
| 2005/0283231 A1 | 12/2005 | Haug et al. | | 623/2.11 |
| 2006/0135964 A1 | 6/2006 | Vesely | | 606/108 |
| 2006/0136052 A1 | 6/2006 | Vesely | | 623/2.18 |
| 2006/0195180 A1 | 8/2006 | Kheradvar et al. | | 623/2.11 |
| 2006/0259134 A1 | 11/2006 | Schwammenthal et al. | | 623/2.11 |
| 2006/0287717 A1 | 12/2006 | Rowe et al. | | 623/2.11 |
| 2007/0016288 A1 | 1/2007 | Gurskis et al. | | 623/2.11 |
| 2007/0027535 A1 | 2/2007 | Purdy et al. | | 623/2.18 |
| 2007/0088431 A1 | 4/2007 | Bourang et al. | | 623/2.11 |
| 2007/0260305 A1 | 11/2007 | Drews et al. | | 623/2.11 |
| 2008/0004696 A1 | 1/2008 | Vesely | | 623/2.1 |
| 2008/0033545 A1 | 2/2008 | Bergin et al. | | 326/2.11 |
| 2008/0065011 A1 | 3/2008 | Marchand et al. | | 604/103.02 |
| 2008/0071367 A1 | 3/2008 | Bergin et al. | | 623/2.11 |
| 2008/0082164 A1 | 4/2008 | Friedman | | 623/2.11 |
| 2008/0195199 A1 | 8/2008 | Kheradvar et al. | | 623/2.11 |
| 2008/0228254 A1 | 9/2008 | Ryan | | 623/1.2 |
| 2010/0036484 A1 | 2/2010 | Hariton et al. | | 623/2.18 |
| 2011/0257735 A1 | 10/2011 | Salahieh et al. | | 623/2.11 |
| 2012/0010699 A1 * | 1/2012 | Vesely | | 623/2.11 |
| 2012/0016469 A1 | 1/2012 | Salahieh et al. | | 623/2.11 |
| 2012/0041549 A1 | 2/2012 | Salahieh et al. | | 623/2.11 |
| 2012/0046740 A1 | 2/2012 | Paul et al. | | 623/2.11 |
| 2012/0053683 A1 | 3/2012 | Salahieh et al. | | 623/2.11 |
| 2012/0078354 A1 | 3/2012 | Cohn | | 623/2.11 |

FOREIGN PATENT DOCUMENTS

| | | | | |
|---|---|---|---|---|
| WO | WO 99/53845 | 10/1999 | | A61B 17/64 |
| WO | WO 00/47139 | 8/2000 | | A61F 2/24 |
| WO | WO 02/49540 | 6/2002 | | |
| WO | WO 2006/127756 | 11/2006 | | A61F 2/24 |

(56) References Cited

FOREIGN PATENT DOCUMENTS

| WO | WO 2008/051428 | 5/2008 | A61F 2/14 |
|---|---|---|---|
| WO | WO 2008/088835 | 7/2008 | A61F 2/84 |
| WO | WO 2009/026272 | 2/2009 | A61B 17/32 |

OTHER PUBLICATIONS

European Search Report for European Patent Application No. 05 027 534.6, Feb. 16, 2006.

European Search Report for European Patent Application No. 07 111 254.4, Aug. 22, 2007.

International Search Report for International Application No. PCT/US2008/073565, Nov. 3, 2008.

International Search Report for International Application No. PCT/US2009/56633, Nov. 13, 2009.

* cited by examiner

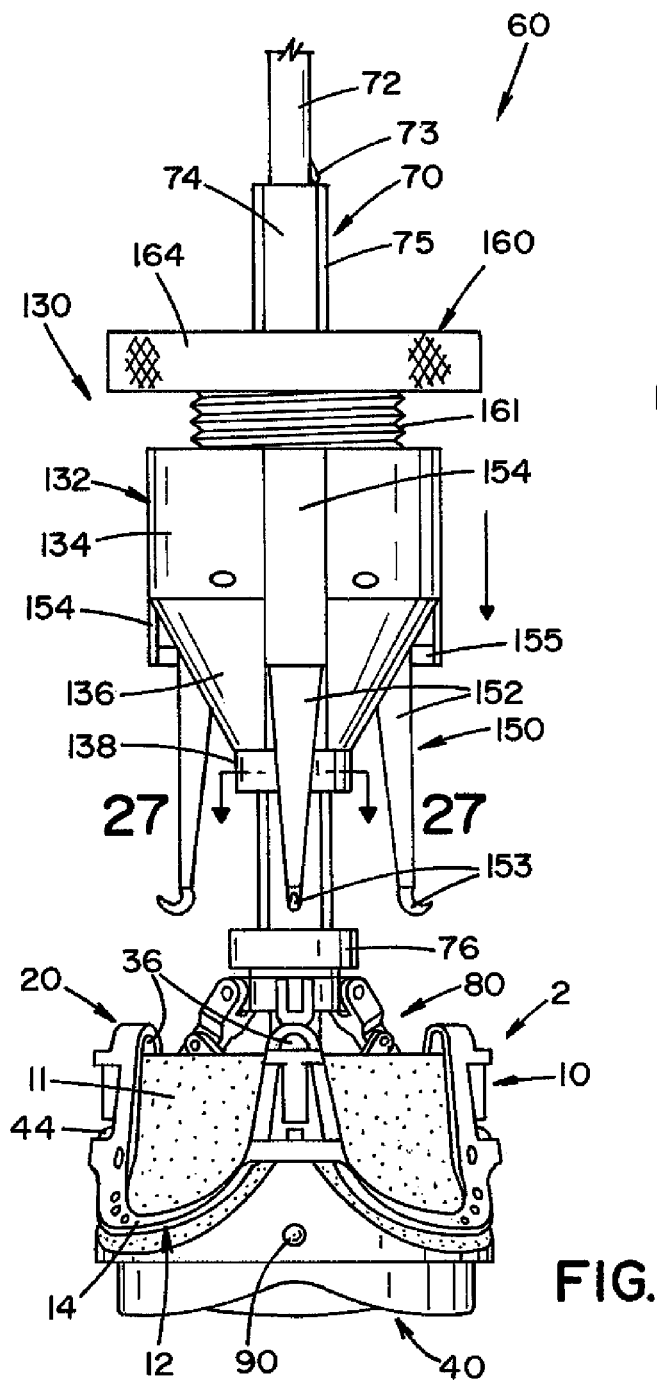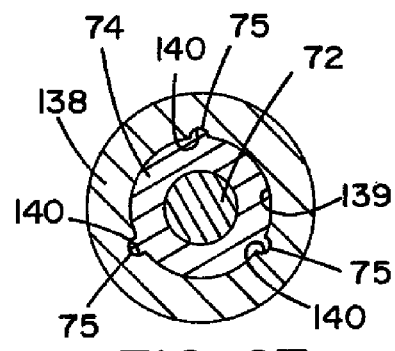
FIG. 26
FIG. 27

US 8,925,164 B2

1

VALVE ASSEMBLY WITH EXCHANGEABLE VALVE MEMBER AND A TOOL SET FOR EXCHANGING THE VALVE MEMBER

RELATED APPLICATION

This application claims the benefit of U.S. Provisional Application No. 61/096,540, filed Sep. 12, 2008, and is fully incorporated herein by reference.

FIELD OF THE INVENTION

The present invention relates generally to the field of cardiovascular valves, and more particularly to a valve assembly including an exchangeable valve member and a docking station, and a tool set that facilitates the removal and installation of the exchangeable valve member.

BACKGROUND OF THE INVENTION

The demographics of patients suffering valvular disease are broad and the treatment modalities for each are complex. Historically, patients younger than 65 years of age have been prescribed mechanical heart valves, while older patients have been prescribed bioprosthetic heart valves that are comprised of biological tissue mounted on a plastic or metallic supporting structure. However, the role of the patient in choosing a particular valve type is changing. In this regard, younger patients that are active now frequently opt for bioprosthetic valves, since such patients are unwilling to deal with the lifestyle changes that are required by mechanical valves and the associated chronic anticoagulation therapy. These patients often prefer undergoing repeat surgeries to replace a worn-out bioprosthetic valve, rather than deal with the lifestyle changes required by mechanical valves.

In view of the need for replacement of bioprosthetic heart valves, a cardiovascular valve assembly has been developed comprising an exchangeable valve member, including a leaflet component, and a docking station (also referred to herein as a "base member"). The docking station is permanently installed, and the valve member is detachably mounted or engaged with the docking station to allow exchange of the valve member. Accordingly, this two-piece valve assembly enables a valve member having a worn-out leaflet component to be exchanged without requiring open-heart surgery and long periods on cardiopulmonary bypass.

The present invention is directed to an improved cardiovascular valve assembly and a tool set for facilitating the removal and installation of an exchangeable valve member.

SUMMARY OF THE INVENTION

In accordance with one aspect of the present invention, there is provided a multi-function valve exchange apparatus for facilitating exchange of a valve member of a valve assembly that includes a valve member detachably coupled to a base member, the apparatus comprising a holding tool that includes: a first engagement member moveable between a collapsed position and an expanded position, wherein said first engagement member engages with the base member in the expanded position; and first and second sliding members moveable relative to each other to move the first engagement member between the collapsed and expanded positions.

In accordance with another aspect of the present invention, there is provided a multi-function valve exchange apparatus for facilitating exchange of a valve member of a valve assembly that includes a valve member detachably coupled to a base

2 member, the apparatus comprising: (a) a holding tool that includes: a first engagement member moveable between a collapsed position and an expanded position, wherein said first engagement member engages with the base member in the expanded position; and first and second sliding members moveable relative to each other to move the first engagement member between the collapsed and expanded positions; and (b) a removal tool mountable to said holding tool and moveable relative thereto, said removal tool including: a second engagement member moveable between a collapsed position and an expanded position, wherein said second engagement member engages with the valve member of said valve assembly in the expanded position to uncouple said valve member from said base member.

In accordance with still another aspect of the present invention, there is provided a multi-function valve exchange apparatus for facilitating exchange of a valve member of a valve assembly that includes a valve member detachably coupled to a base member, the apparatus comprising: (a) a holding tool that includes: a first engagement member moveable between a collapsed position and an expanded position, wherein said first engagement member engages with the base member in the expanded position; and first and second sliding members moveable relative to each other to move the first engagement member between the collapsed and expanded positions; and (b) an insertion tool mountable to said holding tool and moveable relative thereto, wherein said insertion tool includes: a guide sleeve for guiding movement of the insertion tool relative to said holding tool; and a second engagement member attached to the guide sleeve, wherein a new valve member is attachable to the third engagement member.

In accordance with yet another aspect of the present invention, there is provided a multi-function valve exchange apparatus for facilitating exchange of a valve member of a valve assembly that includes a valve member detachably coupled to a base member, the apparatus comprising: (a) a holding tool that includes: a first engagement member moveable between a collapsed position and an expanded position, wherein said first engagement member engages with the base member in the expanded position; and first and second sliding members moveable relative to each other to move the first engagement member between the collapsed and expanded positions; and (b) an alignment tool mountable to the holding tool and moveable relative thereto, wherein said alignment tool includes: a collar portion; and a second engagement member comprising: a plurality of arms extending from the collar portion; and a plurality of caps for engagement with said valve member of said valve assembly, wherein each cap is connected with one of said arms.

In accordance with still another aspect of the present invention, there is provided a multi-function valve exchange apparatus for facilitating exchange of a valve member of a valve assembly that includes a valve member detachably coupled to a base member, the apparatus comprising: (a) a holding tool including: a first engagement member moveable between a collapsed position and an expanded position, wherein said first engagement member engages with the base member in the expanded position; and first and second sliding members moveable relative to each other to move the first engagement member between the collapsed and expanded positions; and (b) a removal tool mountable to said holding tool and moveable relative thererto, said removal tool including: a second engagement member moveable between a collapsed position and an expanded position, wherein said second engagement member engages with the valve member of said valve assembly in the expanded position to uncouple said valve member from said base member; and (c) an insertion tool mountable to said holding tool and moveable relative thereto, wherein said insertion tool includes: a guide sleeve for guiding movement of the insertion tool relative to said holding tool; and a third engagement member attached to the guide sleeve, wherein a new valve member is attachable to the third engagement member.

An advantage of the present invention is the provision of a valve assembly comprised of a valve member detachably coupled to a docking station, wherein an existing valve member may be conveniently exchanged with a new valve member.

Another advantage of the present invention is the provision of a tool set for facilitating the extraction of an exchangeable cardiovascular valve member from an installed docking station, wherein the exchangeable cardiovascular valve member is detachably mounted to the docking station.

Another advantage of the present invention is the provision of a tool set for facilitating the installation of an exchangeable cardiovascular valve member, wherein the exchangeable valve member is engaged with an installed docking station.

Still another advantage of the present invention is the provision of a multi-function valve exchange apparatus that facilitates extraction of an exchangeable valve member from an installed docking station, and installation of a replacement exchangeable valve member.

Yet another advantage of the present invention is the provision of a process for removal and installation of an exchangeable valve member.

These and other advantages will become apparent from the following description of embodiments of the present invention taken together with the accompanying drawings and the appended claims.

BRIEF DESCRIPTION OF THE DRAWINGS

The invention may take physical form in certain parts and arrangement of parts, embodiments of which will be described in detail in the specification and illustrated in the accompanying drawings which form a part hereof, and wherein:

FIG. 26 is an elevational view of a removal tool of the multi-function valve exchange apparatus of FIG. 19, illustrating the removal tool being guided into position relative to a valve assembly during the process to exchange the installed valve member;

FIG. 27 is a cross-sectional view of the multi-function valve exchange apparatus taken across lines 27-27 of FIG. 26;

DETAILED DESCRIPTION OF THE INVENTION

Figure 1:
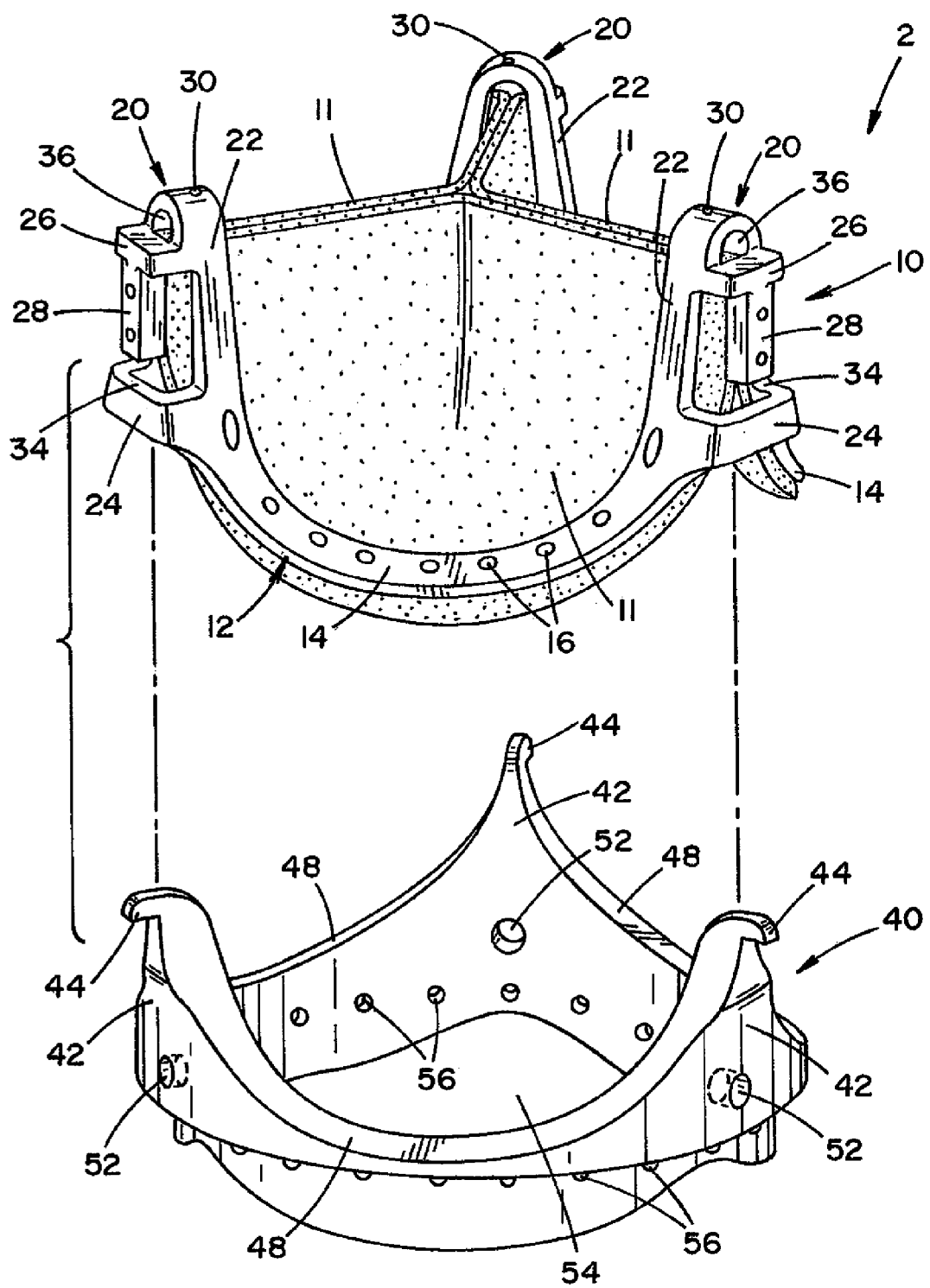
FIG. 1 is an exploded view of a cardiovascular valve assembly, according to an embodiment of the present invention, the valve assembly including an exchangeable valve member and a base member, and adapted for use in connection with the tools of the present invention.
Figure 2:
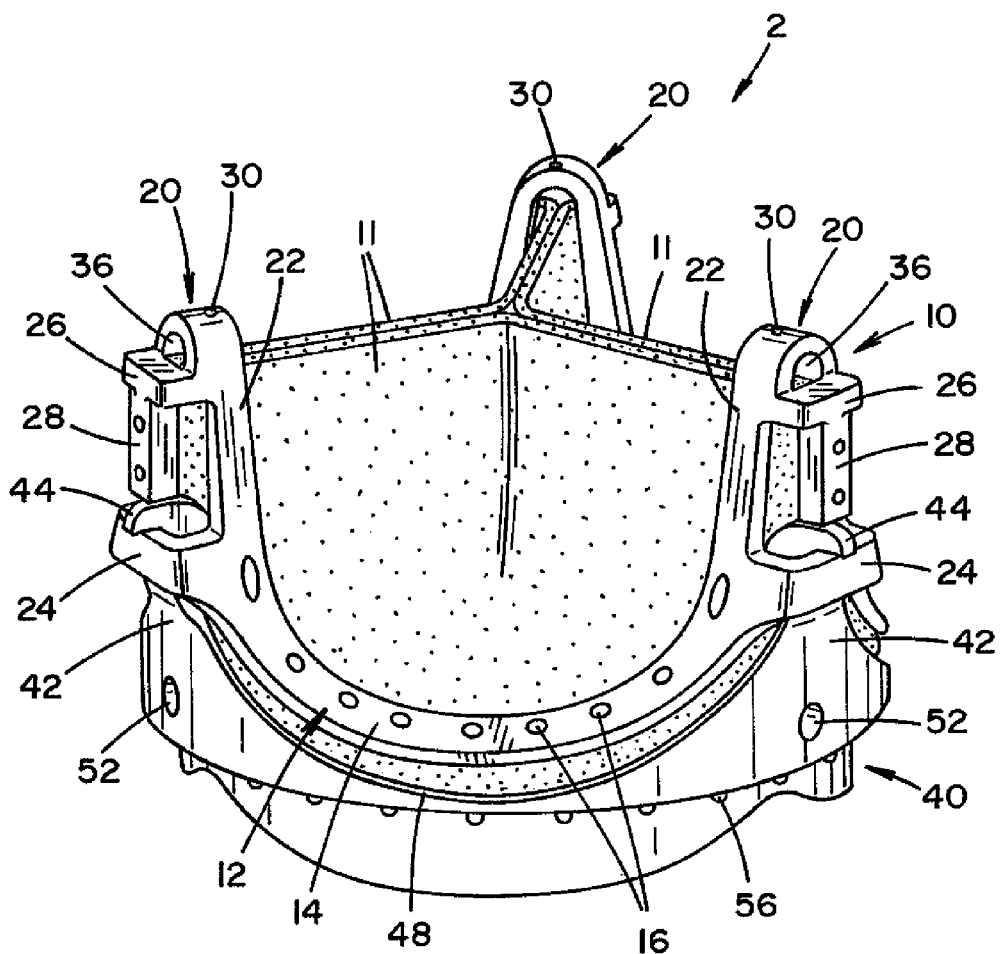
FIG. 2 is a perspective view of the valve assembly of FIG. 1, wherein the valve member is shown coupled to the base member.

Referring now to the drawings wherein the showings are for the purposes of illustrating the present invention only and not for the purposes of limiting same, FIG. 1 shows an exploded view of a cardiovascular valve assembly 2, according to an embodiment of the present invention. Valve assembly 2 is adapted for use in connection with the tool set of the present invention, which is described below. Valve assembly 2 is comprised of a docking station or base member 40 and a valve member 10 that is detachably coupled to base member 40. FIG. 2 shows valve member 10 coupled to base member 40. In the illustrated embodiment, valve member 10 is a bioprosthetic valve. However, it is contemplated that valve member 10 may also take the form of a mechanical valve.

Base member 40 is generally comprised of a plurality of mounting portions 42 and a plurality of arcuate sections 48 located between mounting portions 42. Mounting portions 42 function as stent posts of base member 40. Each mounting portion 42 includes an outward extending protuberance or tab 44. Mounting portions 42 and arcuate sections 48 define a generally cylindrical recess 54. A plurality of recesses 52 are formed in base member 40. Recesses 52 are provided to allow a stabilizer or holding tool to engage and hold base member 40, as will be explained below. Recesses 52 may take the form of a hole or depression formed in base member 40.

A sewing cuff or ring (not shown) made of Dacron®, or other medical grade fabric, is sewn to the outer surface of base member 40 using holes 56 located along the circumference of base member 40. The sewing cuff or ring permanently attaches base member 40 to the tissue of the heart. The sewing cuff may also include a sleeve (not shown) to provide further coverage of the outer surface of base member 40.

Valve member 10 is generally comprised of a frame 12 and a plurality of valve leaflets 11 (i.e., a leaflet set) supported by frame 12. Frame 12 includes a plurality of ribbon sections 14 and coupling elements 20. Coupling elements 20 function as stent posts of valve member 10, and allow valve member 10 to be coupled and uncoupled from base member 40, as will be described below.

Each coupling element 20 is comprised of a generally U-shaped portion 22 having lower and upper crossbars 24, 26 extending across U-shaped portion 22. Upper crossbar 26 is T-shaped and includes a downward extending finger 28. Finger 28 and lower crossbar 24 define a lower slot 34. Upper crossbar 26 and the top section of U-shaped portion 22 define an upper slot 36. A fabric cover (not shown) made of a medical grade cloth may be placed over each coupling element 20. In one embodiment of valve member 10, each coupling element 20 includes an opening 30 in generally U-shaped portion 22.

Each ribbon section 14 has a generally arcuate shape, and extends between coupling elements 20. Ribbon sections 14 have an arcuate shape that matches the profile of arcuate sections 48 of base member 40, thereby forming a seal therebetween when valve member 10 is coupled to base member 40. This seal prevents blood leakage between valve member 10 and base member 40.

Frame 12 is preferably made of a flexible material having suitable elasticity to allow frame 12 to collapse into a tight bundle for convenient removal and exchange of valve member 10 through small incisions or a trocar, and to facilitate the engagement and disengagement of coupling elements 20 and mounting portions 42, as will be described below. In the illustrated embodiment, frame 12 is made of a medical grade polymer material, such as poly-ether-ether-ketone (PEEK), polyurethane or polycarbonate. However, it is also contemplated that frame 12 may alternatively be formed of a metal, including, but not limited to, Elgiloy, nitinol, stainless steel, platinum, gold, titanium, other biocompatible metals, and combinations thereof.

As indicated above, leaflets 11 are supported by frame 12. In this regard, leaflets 11 may be sewn to ribbon sections 14 using holes 16 formed along the length of ribbon sections 14. Alternatively, leaflets 11 may be attached to ribbon sections 14 by appropriate means, such as sutures, clips, staples or other fastening devices. Leaflets 11 may be made of suitable materials, including, but not limited to, bovine pericardium, equine pericardium, ovine pericardium, porcine aortic valve tissue, small intestinal submucosa (SIS), various biodegradable substrates for tissue engineered valves, and various relatively inert polymers, such as polyurethane. In order to improve clarity, leaflets 11 have been omitted from some figures illustrating the present invention.

Figure 3:
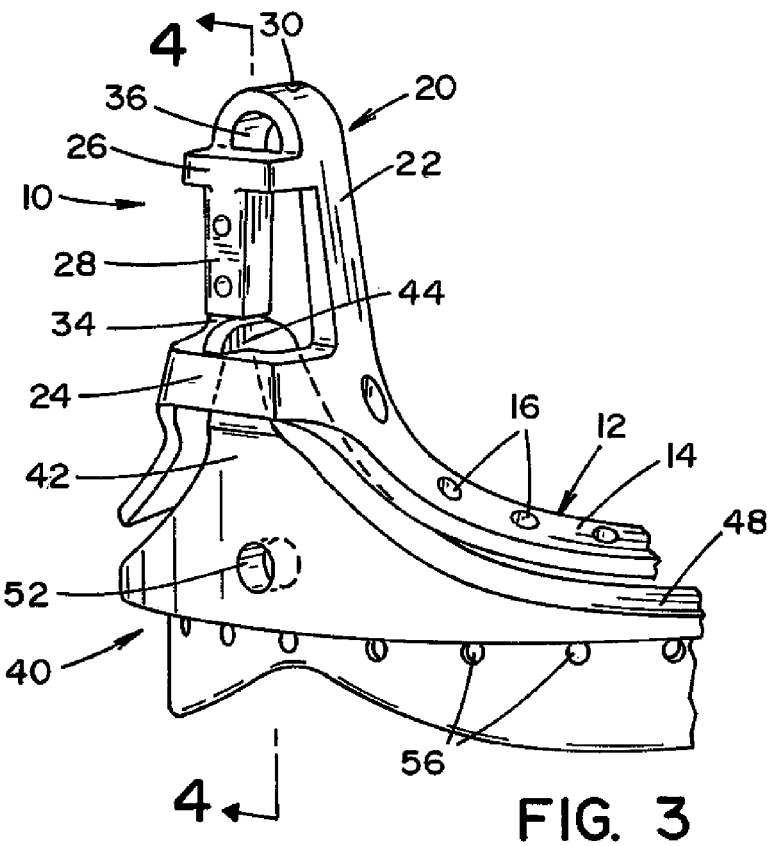
FIG. 3 is an enlarged view of a portion of the valve assembly, showing a coupling element of the valve member engaged with a mounting portion of the base member.
Figure 4:
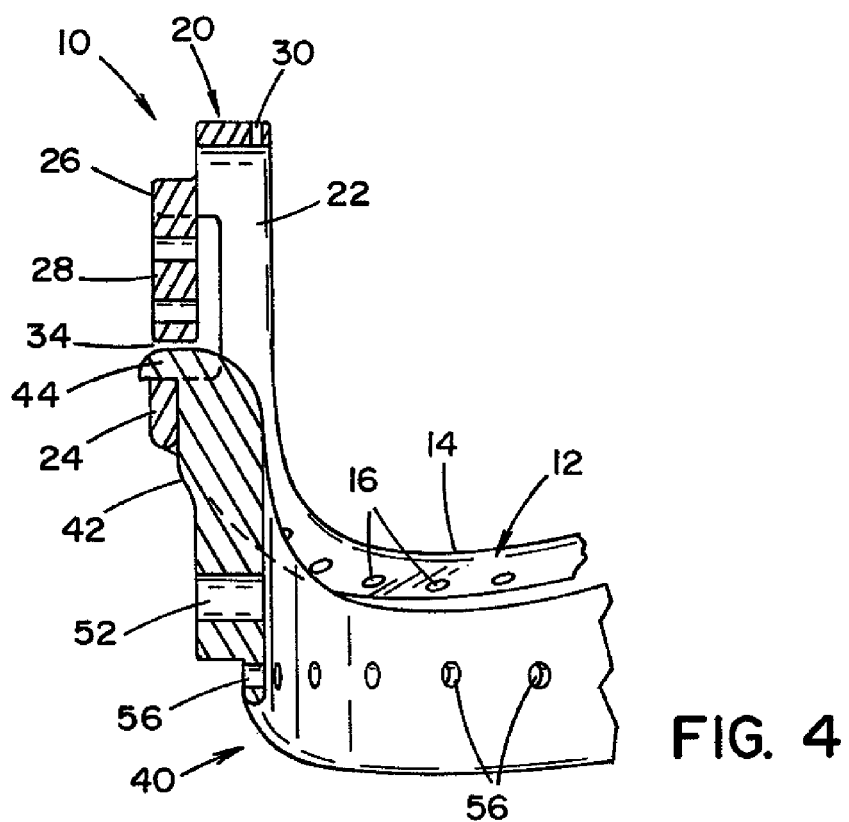
FIG. 4 is a cross-sectional view taken along lines 4-4 of FIG. 3.

In the illustrated embodiment of the present invention, each pair of mounting portion 42/coupling element 20 provides a protuberance-slot mechanism, as best seen in FIGS. 3 and 4. However, it is also contemplated that the configuration may be reversed, wherein each coupling element 20 provides a protuberance and each mounting portion 42 provides a slot. The entire protuberance-slot mechanism is covered by a cap (not shown) that prevents fibrotic ingrowth. All exposed surfaces of valve assembly 2 are preferably covered by a fabric cover (not shown) made of Dacron®, or other medical grade fabric, as in conventional bioprosthetic valves.

Valve member 10 is coupled and uncoupled to/from base member 40 through engagement and disengagement of coupling elements 20 and mounting portion 42. In the illustrated embodiment, lower slot 34 of each coupling element 20 is dimensioned to receive a respective tab 44 of each mounting portion 42, thereby coupling valve member 10 to base member 40. As best seen in FIGS. 3 and 4, tab 44 is captured between the lower surface of finger 28 of upper crossbar 26 and the upper surface of lower crossbar 24. As discussed above, frame 12 is formed of an elastic material. Accordingly, frame 12 is dilated by outward deflection to disengage tab 44 of each mounting portion 42 from lower slot 34 of each coupling element 20. Consequently, valve member 10 is uncoupled from base member 40. Coupling and uncoupling of valve member 10 to/from base member 40 is facilitated by use of the tool set of the present invention, which is described in detail below. Once valve member 10 is coupled to base member 40, valve member 10 is secured such that it cannot unintentionally uncouple from base member 40. In this respect, outward deflection of frame 12 is opposite to normal cardiac forces, thus providing secure engagement.

A multi-function valve exchange apparatus 230 will now be described with reference to FIGS. 5-8. Multi-function valve exchange apparatus 230, according to a first embodiment, is comprised of a stabilizer or holding tool 232 for holding base member 40 during a valve exchange procedure and a valve extraction or removal tool 234 for removing an existing valve member 10 from an installed base member 40. Multi-function valve exchange apparatus 230 may also include a valve insertion tool 400 for facilitating the installation of a replacement valve member 10. Valve insertion tool 400 will be described below with reference to FIGS. 15-18. In the illustrated embodiment, multi-function valve exchange apparatus 230 also includes first and second actuator tools 180 and 220 (FIG. 5) for actuation of multi-function valve exchange apparatus 230. First and second actuator tools 180 and 220 are described below.

Figure 6:
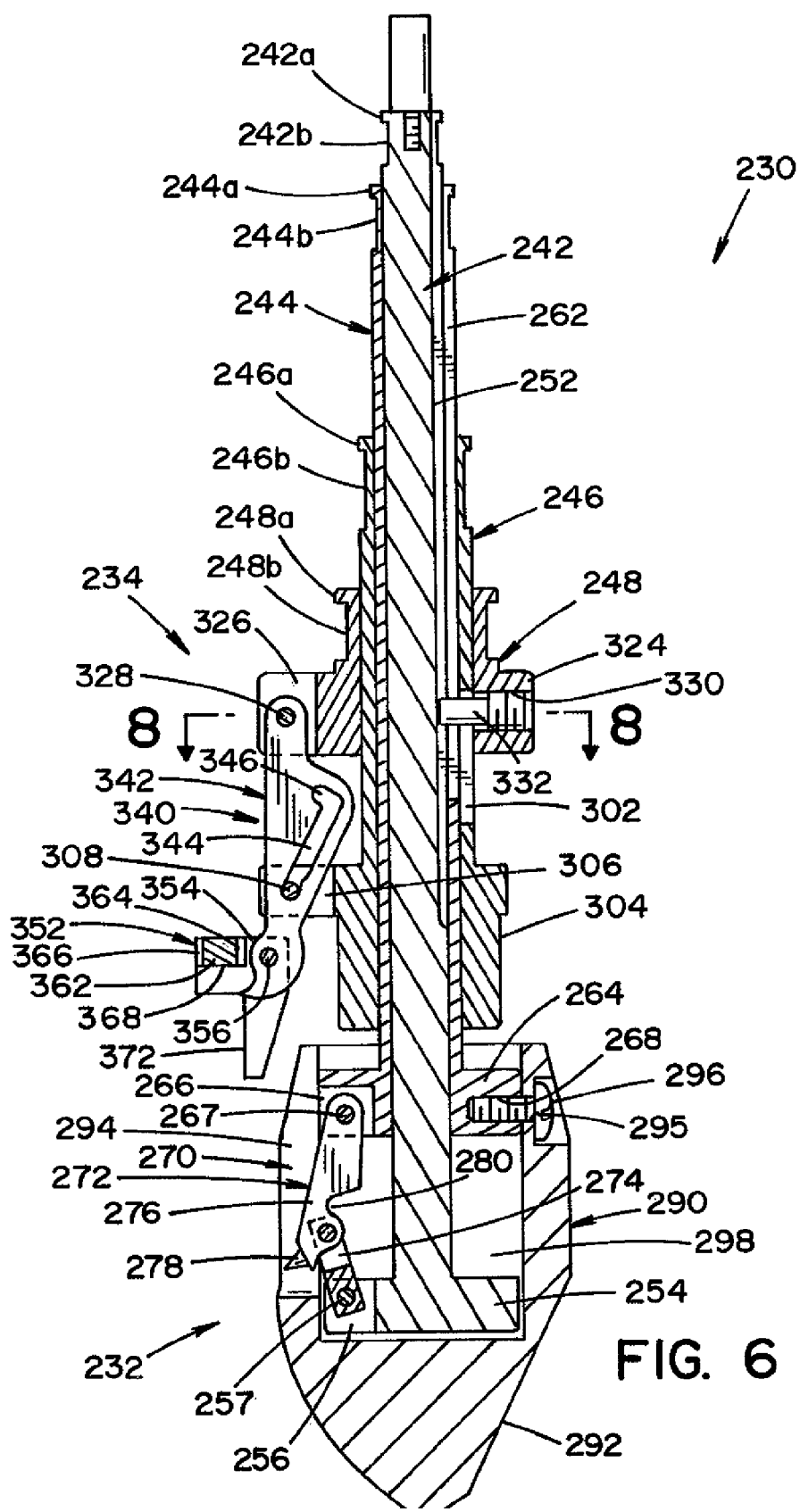
FIG. 6 is a cross-sectional view of the holding tool and the removal tool of the multi-function valve exchange apparatus shown in FIG. 5, wherein the holding and removal tools are shown in their respective collapsed positions.
Figure 7:
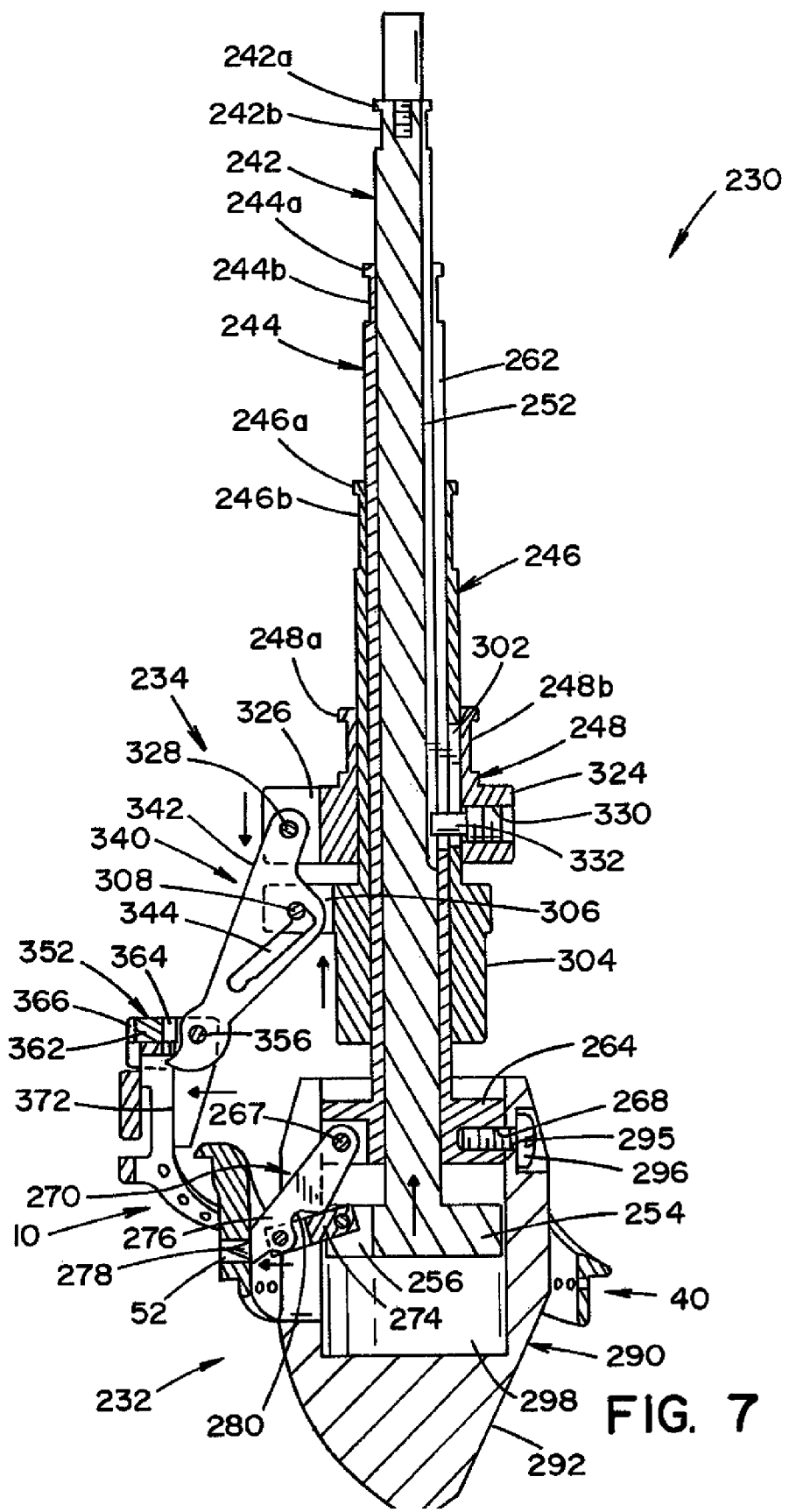
FIG. 7 is a cross-sectional view of the holding tool and the removal tool of the multi-function valve exchange apparatus, wherein the holding and removal tools are shown in their respective expanded positions, in relation to a cardiovascular valve assembly.

Holding tool 232 and removal tool 234 will now be described with reference to FIGS. 6-8. Holding tool 232 is generally comprised of a first elongated sliding member 242, a second elongated sliding member 244, an engagement member 270 and a nose cone 290. Removal tool 234 is generally comprised of a third elongated sliding member 246, a fourth sliding member 248, and an engagement member 340. Sliding members 242, 244, 246 and 248 are arranged to nest within each other in a telescoping manner, as seen in FIGS. 6 and 7.

In the illustrated embodiment of holding tool 232, first sliding member 242 generally takes the form of a cylindrical rod having a first annular hub portion 254 at one end thereof. A slot 252 extends along a portion of the length of the rod. Slot 252 is open at one end of first sliding member 242. An annular channel 242b that defines an annular flange 242a is located at one end of first sliding member 242. Annular channel 242b is used in connection with the actuator tools described below. A plurality of slots 256 are formed in first hub portion 254. Pins 257 extend across slots 256.

According to the illustrated embodiment of the present invention, second sliding member 244 generally takes the form of a tubular sleeve having a second annular hub portion 264. Second sliding member 244 is dimensioned to receive first sliding member 242 such that first sliding member 242 is moveable relative to second sliding member 244. A slot 262 extends along a portion of the length of the sleeve. Slot 262 is open at one end of second sliding member 244. An annular channel 244b that defines an annular flange 244a is located at one end of second sliding member 244. Annular channel 244b is used in connection with the actuator tools described below. A plurality of slots 266 are formed in second hub portion 264. Pins 267 extend across slots 266. A threaded recess 268 is formed in hub portion 264 generally transverse to the longitudinal axis of second sliding member 244.

Engagement member 270 includes a plurality of articulating joints 272. Each joint 272 is comprised of a link 274 and an arm 276. A projection 278 extends outward from one end of arm 276, as seen in FIGS. 6 and 7. Projection 278 is dimensioned to be received by recesses 52 of base member 40, as will be described below. It should be appreciated that projections 278 may have alternative shapes from the illustrated embodiment. Arm 276 also includes a recess 280 to lock engagement member 270 in an expanded position, as will be explained below with reference to FIG. 7.

A first end of link 274 is pivotally connected with first hub portion 254 of first sliding member 242, and a second end of link 274 is pivotally connected with a first end of arm 276. Each slot 256 of first hub portion 254 is dimensioned to receive one end of a link 274. The second end of arm 276 is pivotally connected with second hub portion 264 of second sliding member 244. Each slot 266 of second hub portion 264 is dimensioned to receive one end of an arm 276.

Nose cone 290 has a generally conical face 292 and an inner cavity 298. Conical face 292 facilitates insertion of valve exchange apparatus 230 through leaflets 11 of valve member 10, thereby allowing valve exchange apparatus 230 to be properly located relative to valve assembly 2 during a process for exchanging a valve member 10, as will be described below. Openings 295 formed in nose cone 290 are dimensioned to receive fasteners 296 (e.g., screws) for attaching nose cone 290 to second hub portion 264 of second sliding member 244. Inner cavity 298 is dimensioned to receive first hub portion 254 of first sliding member 242. Slots 294 are formed in nose cone 290, and are dimensioned to allow free movement of articulating joints 272.

As first sliding member 242 is moved relative to second sliding member 244, engagement member 270 moves between a collapsed position (FIG. 6) and an expanded position (FIG. 7). In the expanded position, projections 278 of arms 276 are received by recesses 52 of base member 40 in order to engage holding tool 232 therewith, as shown in FIG. 7. In the expanded position, a portion of each link 274 is received into recess 280 of arm 276, thereby locking engagement member 270 in the expanded position.

As mentioned above, removal tool 234 is generally comprised of a third elongated sliding member 246, a fourth sliding member 248, and an engagement member 340.

In the illustrated embodiment of removal tool 234, third sliding member 246 generally takes the form of a tubular sleeve having a third annular hub portion 304 at one end thereof. A slot 302 extends along a portion of the length of the sleeve. Slot 302 is closed at both ends thereof. An annular channel 246b that defines an annular flange 246a is located at one end of third sliding member 246. Annular channel 246b is used in connection with the actuator tools described below. A plurality of slots 306 are formed in third hub portion 304. A pin 308 extends across each slot 306.

According to the illustrated embodiment of the present invention, fourth sliding member 248 generally takes the form of a tubular collar having a fourth annular hub portion 324. Fourth sliding member 248 is dimensioned to receive third sliding member 246 such that fourth sliding member 248 is moveable relative to third sliding member 246. Furthermore, third sliding member 246 is dimensioned to receive first and second sliding members 242, 244 such that removal tool 234 is moveable relative to holding tool 232, as will be described below.

An annular channel 248b that defines an annular flange 248a is located at one end of fourth sliding member 248. Annular channel 248b is used in connection with actuator tools described below.

A plurality of slots 326 are formed in fourth hub portion 324, and a pin 328 extends across each slot. A threaded channel 330 is formed in the fourth annular hub portion 324 generally transverse to the longitudinal axis of fourth sliding member 248. Threaded channel 330 is dimensioned to receive an alignment pin 332 that extends through elongated slots 252, 262 and 302 in order to properly orient first, second, third and fourth sliding members 242, 244, 246, 248 relative to each other, as best seen in FIG. 8. Elongated slots 252 and 262 are open at one end to allow removal tool 234 to be dismounted from holding tool 232, as will be explained below.

Engagement member 340 is generally comprised of a plurality of arms 342 and generally L-shaped caps 352. A first end of arm 342 is pivotally mounted to fourth hub portion 324 of fourth sliding member 248. Each arm 342 includes an L-shaped slot 344 dimensioned to receive pin 308 of third sliding member 246. End 346 of L-shaped slot 344 captures pin 308 to lock engagement member 340 in an expanded position.

Figure 8:
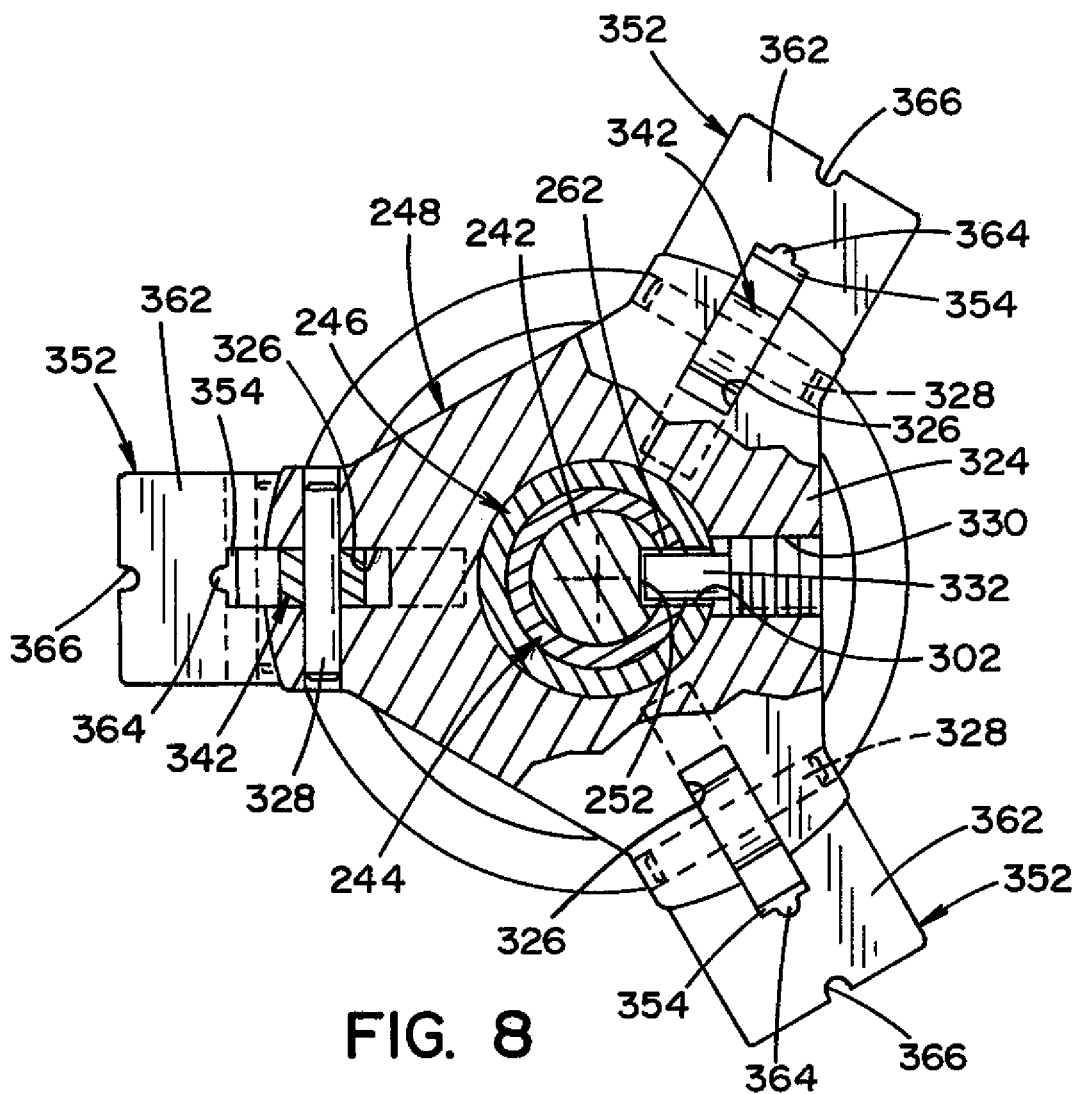
FIG. 8 is a cross-sectional view taken along lines 8-8 of FIG. 6.

Cap 352 includes a slot 354, as best seen in FIG. 8. A pin 356 is located across slot 354 to pivotally mount cap 352 to arm 342. As shown in FIG. 8, cap 352 includes an outward extending body 362 and a pair of downward extending fingers 372. Body 362 has a curved inner surface 368 that generally matches the surface profile of upper surface of U-shaped portion 22 of valve member 10 (see FIG. 10). With reference to FIG. 8, a recess 364 is formed in body 362 adjacent to slot 354, and a notch 366 is formed in the outer surface of body 362.

As third sliding member 246 is moved relative to fourth sliding member 248, engagement member 340 moves between a collapsed position (FIG. 6) and an expanded position (FIG. 7). In the expanded position, caps 352 are engaged with coupling elements 20 of valve member 10, as will be explained in detail below. Arms 342 are locked in position when engagement member 340 is moved to the fully expanded position. In this respect, pin 308 of third hub portion 304 is captured within end 346 of L-shaped slot 344, as shown in FIG. 7.

Figure 16:
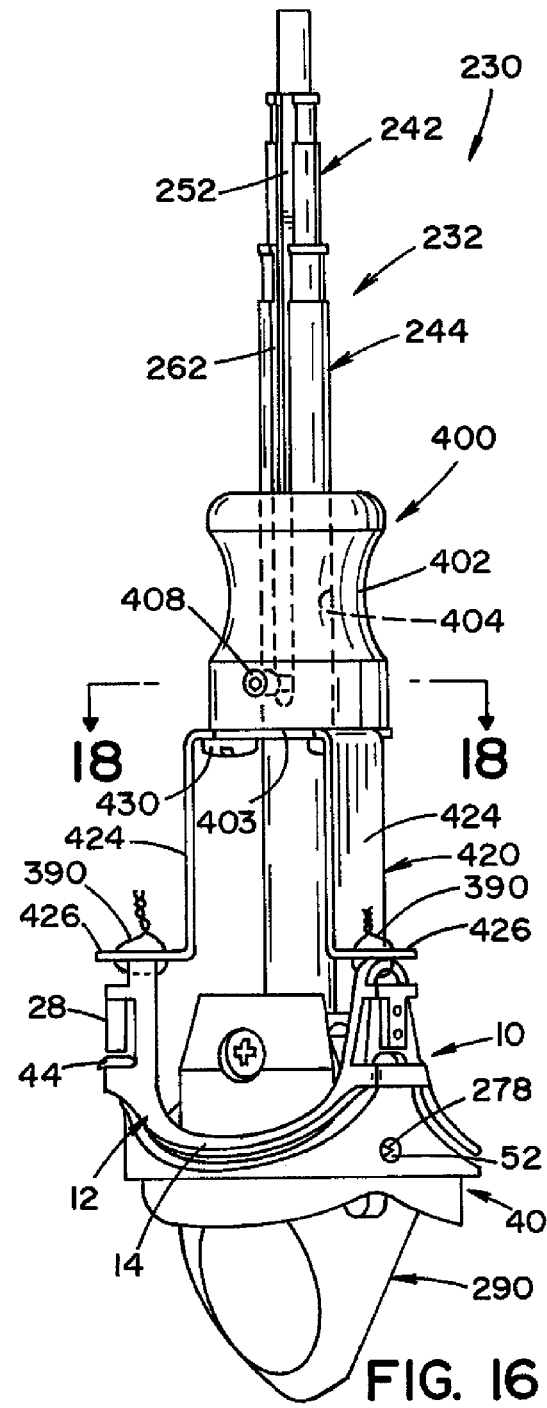
FIG. 16 is an elevation view of the multi-function valve exchange apparatus shown in FIG. 15, illustrating the insertion tool coupling the new valve member to the installed base member.
Figure 17:
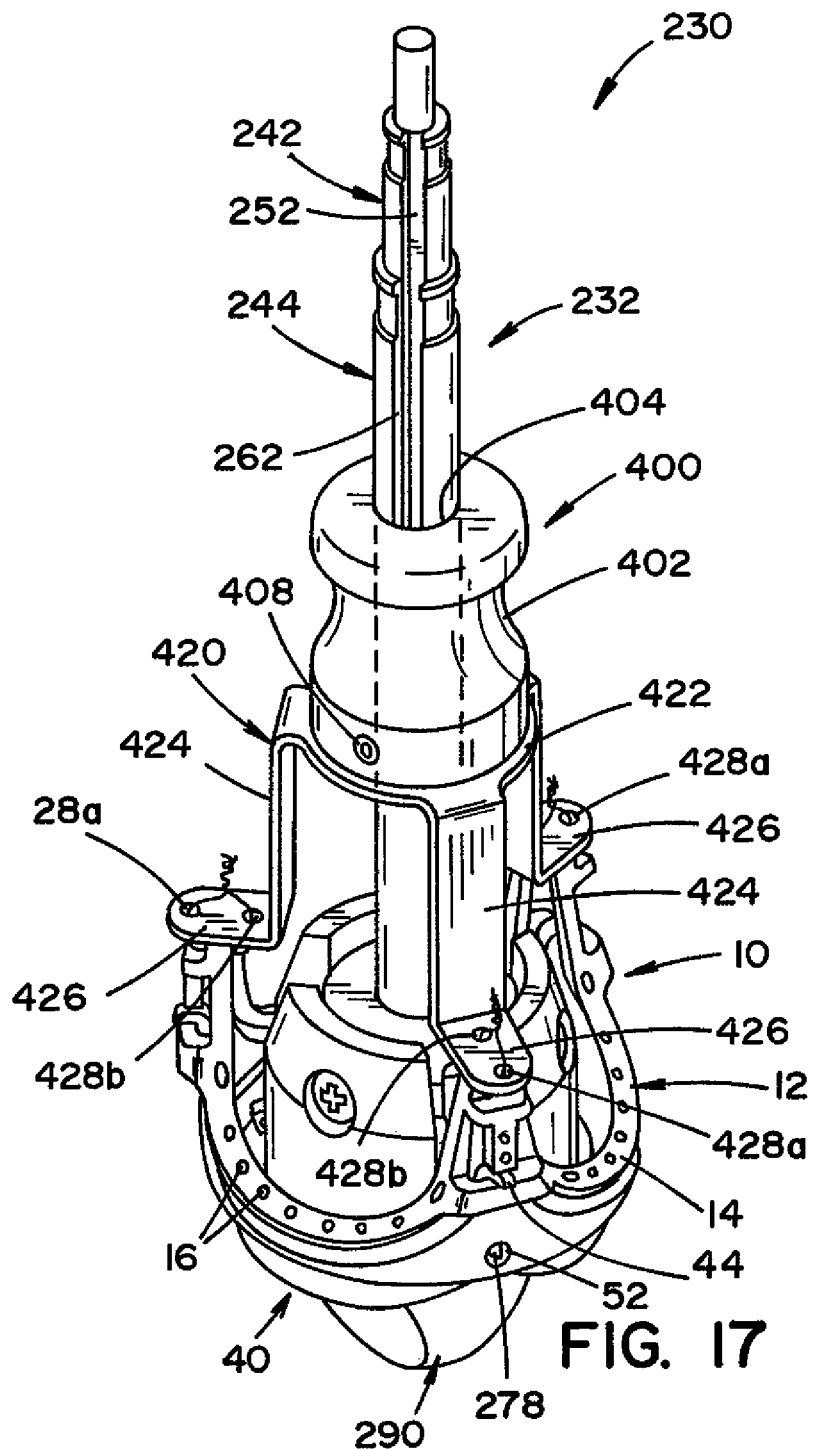
FIG. 17 is a perspective view of the multi-function valve exchange apparatus shown in FIG. 15, illustrating the insertion tool coupling the new valve member to the installed base member.
Figure 18:
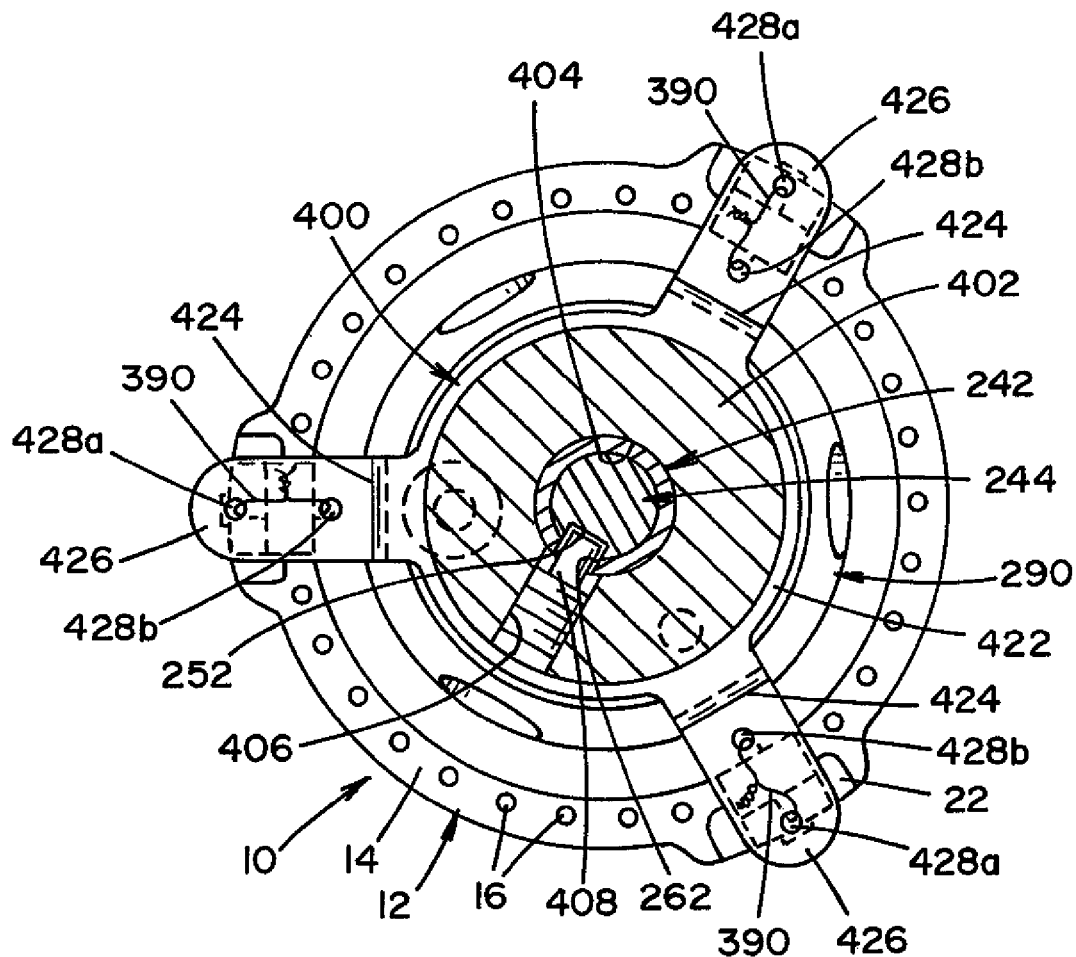
FIG. 18 is a cross-sectional view taken across lines 18-18 of FIG. 16.

Valve insertion tool 400 will now be described with reference to FIGS. 15-18. Valve insertion tool 400 is generally comprised of a tubular collar or guide sleeve 402 and an engagement member 420. Guide sleeve 402 includes a cylindrical recess 404 extending along the longitudinal axis thereof. Cylindrical recess 404 is dimensioned to receive first and second sliding members 242, 244 of holding tool 232, such that valve insertion tool 400 is moveable relative to holding tool 232. A threaded opening 406 extends through guide sleeve 402 generally transverse to cylindrical recess 404. An alignment pin 408 is threaded into opening 406 and extends into cylindrical recess 404. Elongated slots 252 and 262 of first and second sliding members 242, 244 are dimensioned to receive alignment pin 408, as shown in FIG. 18.

In the illustrated embodiment of insertion tool 400, engagement member 420 takes the form of a bracket having a mounting base 422, a plurality of legs 424, and a plurality of feet 426 respectively extending outward from each of the legs 424. A pair of holes 428a, 428b are formed in each of the legs 424. Base 422 is mounted to lower surface 403 of guide sleeve 402 using a plurality of fasteners 430. In the illustrated embodiment, fasteners 430 are screws. It is also contemplated that engagement member 420 may be integrally formed with guide sleeve 402 as a unitary component.

First actuator tool 180 will now be described with reference to FIG. 5. In the illustrated embodiment, actuator tool 180 resembles a conventional surgical forceps. Actuator tool 180 generally comprises a pair of elongated arms (first arm 182 and second arm 184), a first attachment plate 200 and a second attachment plate 210.

First and second arms 182, 184 are pivotally connected to one another in a scissors-like fashion by a pivotal connection 190, such as a box or mortise type joint, as well known in the art. First and second arms 182, 184 have first and second finger grips 186, 188 at a proximal end thereof, and have first and second jaws 192, 194 at a distal end thereof, respectively. In the illustrated embodiment of actuator tool 180, first jaw 192 has a shorter length than second jaw 194. First and second arms 182, 184 respectively include catches 187 and 189 that engage each other, so as to prevent separation of first and second grips 186, 188 until a user applies a twisting movement in order to separate catches 187, 189 from each other.

First attachment plate 200 is attached to the distal end of first jaw 192, and second attachment plate 210 is attached to the distal end of second jaw 194. In the illustrated embodiment, first attachment plate 200 has a pair of spaced-apart upward-extending side walls 204a, 204b that define a gap 206 therebetween. Holes 205 are formed in side walls 204a, 204b to allow attachment plate 200 to be attached to the distal end of first jaw 192. The free end of attachment plate 200 has a forked portion 202 that defines a slot 203. Gap 206 of first attachment plate 200 is dimensioned to allow second jaw 194 to extend therethrough. Second attachment plate 210 is connected to the distal end of second jaw 194 by fasteners. The free end of attachment plate 210 has a forked portion 212 that defines a slot 213. First and second attachment plates 200, 210 are attached to respective jaws 192, 194 such that slots 203 and 213 are generally aligned with each other, as shown in FIG. 5.

In operation of first actuator tool 180, movement of first and second grips 186, 188 toward each other results in the movement of forked portions 202, 212 away from each other. Likewise, movement of first and second grips 186, 188 away from each other results in the movement of forked portions 202, 212 toward each other.

Figure 5:
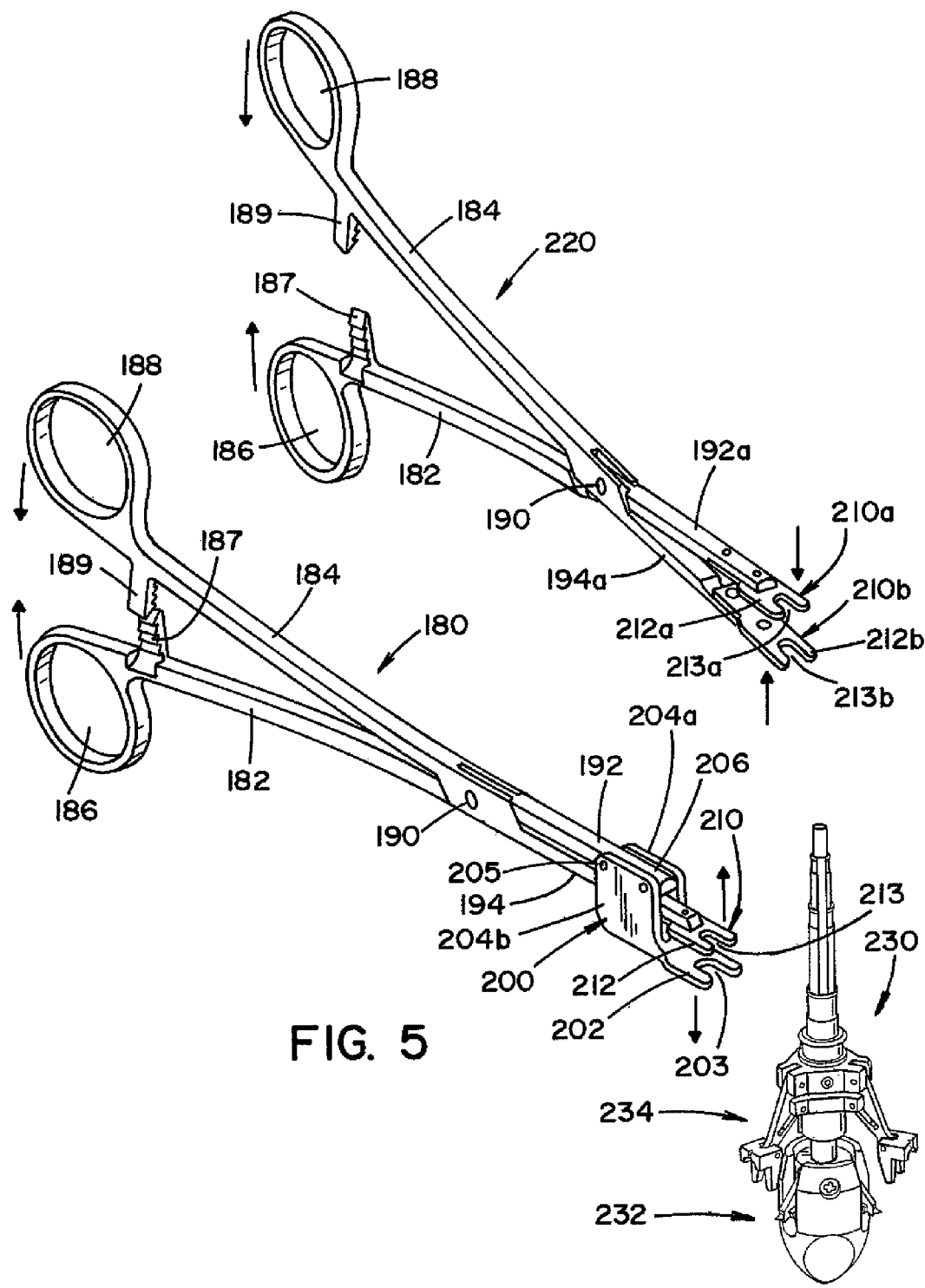
FIG. 5 is a perspective view of components of a multi-function valve exchange apparatus, which includes a holding tool, a removal tool and actuator tools, in accordance with a first embodiment of the present invention.

Second actuator tool 220 shown in FIG. 5 is similar in many respects to first actuator tool 180. Accordingly, similar components of second actuator tool 220 have the same reference numbers as like components of first actuator tool 180. In this embodiment of the actuator tool, first and second jaws 192a, 194a have substantially the same length. Attachment plates 210a, 210b having forked portions 212a, 212b are respectively attached to the distal end of each jaw 192a, 194a, such that the pair of slots 213a, 213b are generally aligned with each other, as shown in FIG. 5.

In operation of second actuator tool 220, movement of first and second grips 186, 188 toward each other results in the movement of the pair of forked portions 212a, 212b towards each other. Likewise, movement of first and second grips 186, 188 away from each other results in the movement of the pair of forked portions 212a, 212b away from each other. Accordingly, second actuator tool 220 operates in a manner opposite to first actuator tool 180, wherein movement of first and second grips 186, 188 towards each other results in movement of forked portions 202, 212 away from each other.

A method for exchanging valve member 10 of an installed valve assembly 2 and the detailed operation of multi-function valve exchange apparatus 230 will now be described in detail with particular reference to FIGS. 9-17.

Figure 9:
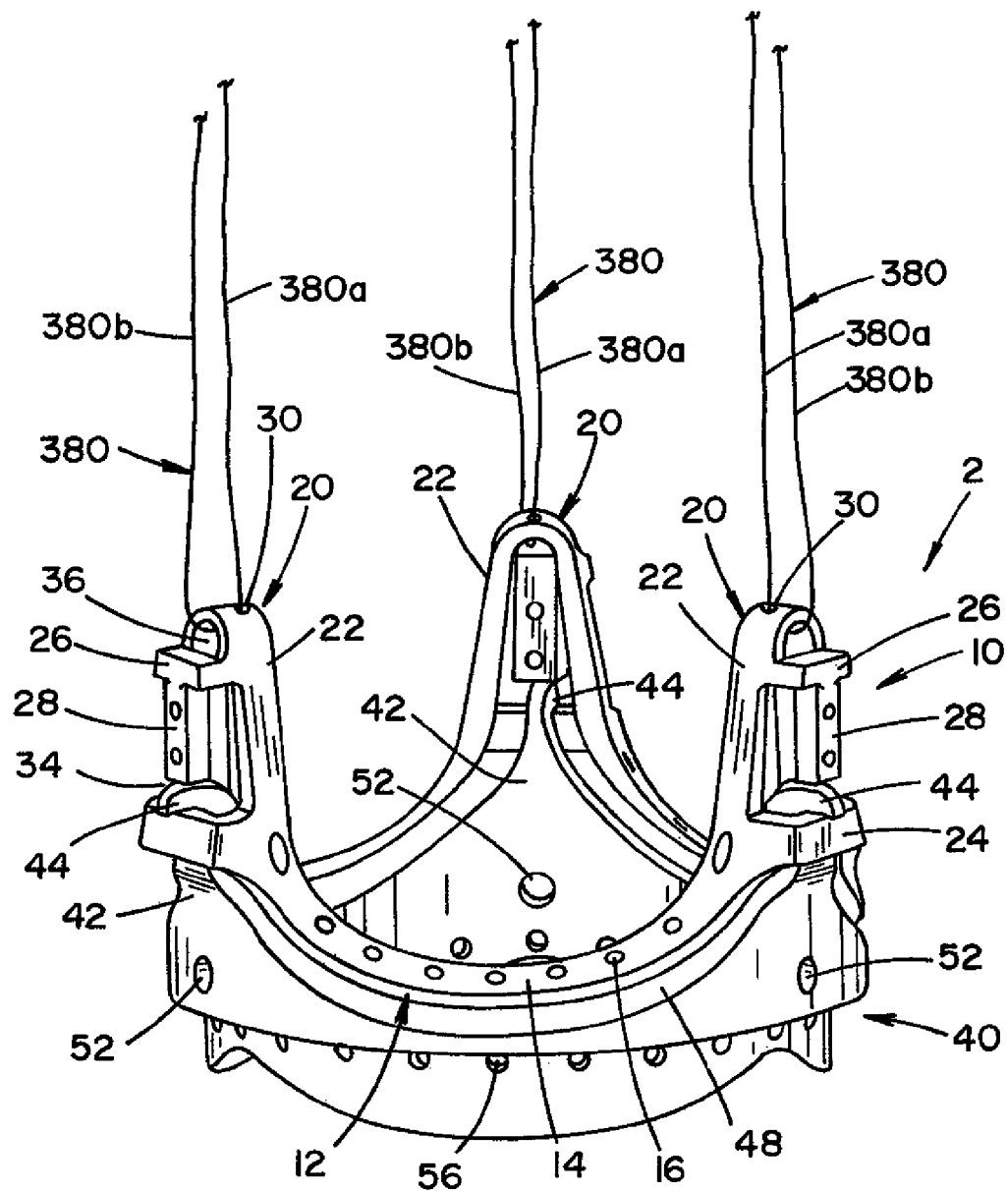
FIG. 9 is a perspective view of the valve assembly illustrating sutures attached thereto for guiding and locating the multi-function valve exchange apparatus to a position relative to the valve assembly, during a process for exchanging a valve member.

According to the illustrated embodiment of the present invention, the method for exchanging valve member 10 includes threading a suture 380 through each opening 30 and upper slot 36 of valve member 10, as shown in FIG. 9. A needle (not shown) may be used to facilitate threading of sutures 380. Sutures 380 are guide wires that function as alignment guide means for locating holding tool 230 in a proper position relative to base member 40 of valve assembly 2, as will be discussed below. In a preferred embodiment, sutures 380 are stainless steel sutures.

Removal tool 234 is mounted onto holding tool 232. In this regard, removal tool 234 is positioned such that alignment pin 332 is aligned with elongated slots 252 and 262 of first and second sliding members 242, 244, as shown in FIG. 8.

Figure 10:
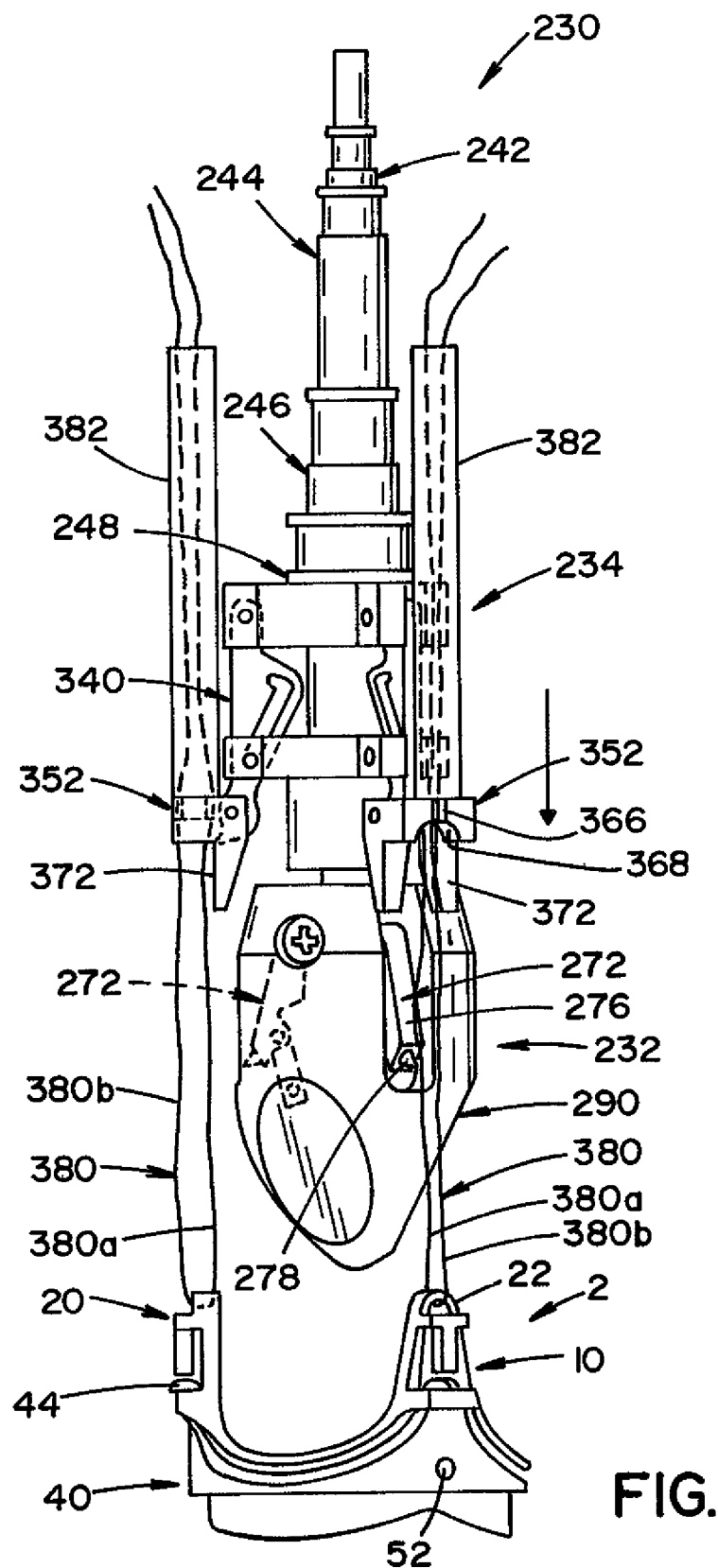
FIG. 10 is an elevational view illustrating the holding tool and the removal tool of the multi-function valve exchange apparatus, as guided into position relative to the valve assembly.

Referring now to FIG. 10, end 380a of each suture 380 is respectively threaded through recess 364 of caps 352 of removal tool 234, and end 380b of each suture 380 is respectively guided through notch 366 of caps 352 of removal tool 234. Recess 364 and notch 366 of caps 352, are best seen in FIG. 8. Ends 380a, 380b of each suture 380 are inserted through a respective tube 382, as shown in FIG. 10. In a preferred embodiment, tubes 382 are made of a plastic material and have a length of about 10 inches (25.4 cm).

Figure 11:
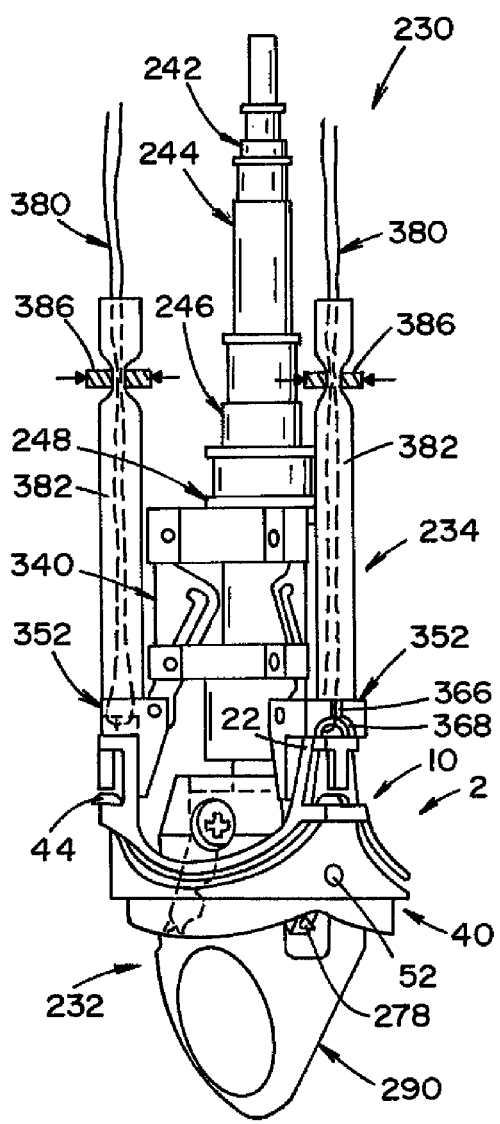
FIG. 11 is an elevational view of the multi-function valve exchange apparatus of FIG. 10, illustrating the removal tool in engagement with the valve assembly.

Apparatus 230 is guided along threaded sutures 380 to properly locate apparatus 230 relative to valve assembly 2. In this regard, apparatus 230 is guided along threaded suture 380 such that curved inner surface 368 each cap 352 respectively abuts the top surface of U-shaped portions 22 of valve member 10, as shown in FIG. 11. When caps 352 abut U-shaped portions 22, apparatus 230 is in an operating position wherein engagement member 270 of holding tool 232 is located proximate to recesses 52 of base member 40. Clamp means 386 are applied to each tube 382 once apparatus 230 is located at the operating position and tubes 382 are located relative to removal tool 234 such that tubes 382 abut the upper surface of caps 352. Application of clamp means 386 to tubes 382 restricts movement of caps 352 relative to valve member 10.

Figure 12:
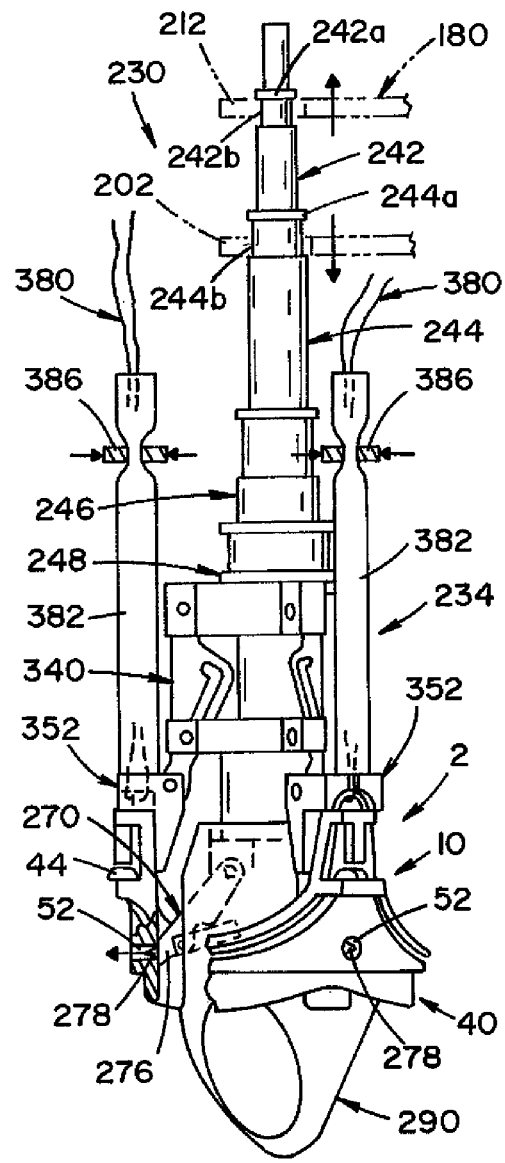
FIG. 12 is an elevational view of the multi-function valve exchange apparatus of FIG. 10, illustrating movement of the holding tool to an expanded position for engagement with the base member.

Next, first actuator tool 180 is engaged with holding tool 232. More specifically, forked portions 202, 212 capture the outer surface of first and second sliding members 242, 244 within annular channels 242b and 244b, as shown in FIG. 12. It should be appreciated that the location of forked portions 202 and 212 may be reversed with respect to the illustrated embodiment. First and second grips 186, 188 are moved toward each other, thereby moving forked portions 202, 212 away from each other. As a result, first sliding member 242 and second sliding member 244 will slide relative to each other such that channels 242b and 244b move away from each other. Movement of first and second sliding members 242 and 244 in this manner causes engagement member 270 to move from a collapsed position to an expanded position. In the expanded position, projections 278 of arms 276 are received by recesses 52 of base member 40 in order to engage holding tool 232 therewith, as shown in FIG. 12. Accordingly, holding tool 232 is securely engaged with base member 40.

Figure 13:
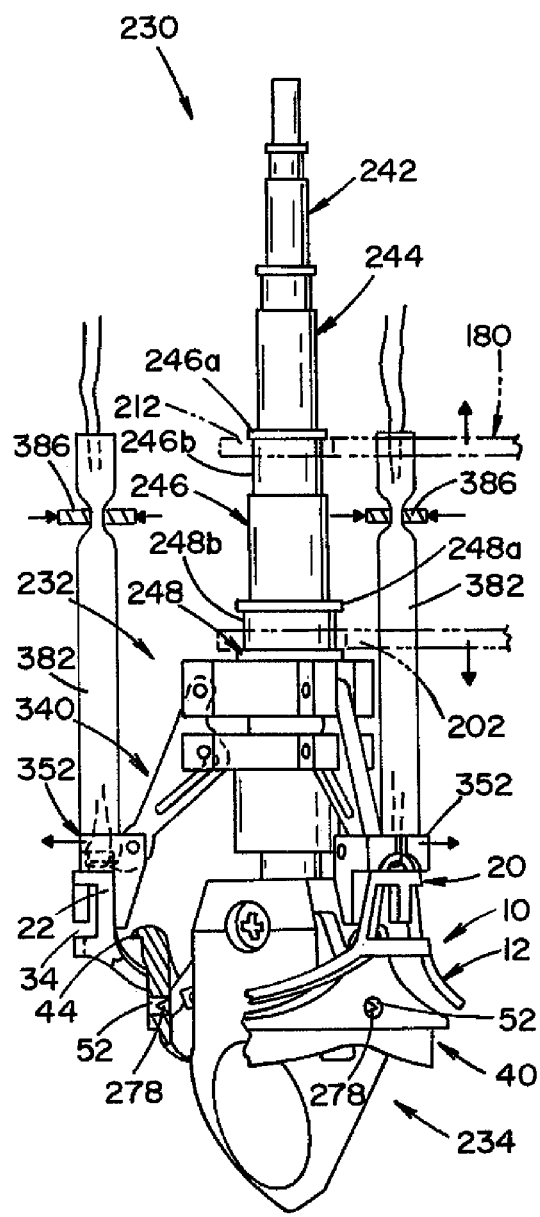
FIG. 13 is an elevational view of the multi-function valve exchange apparatus of FIG. 10, illustrating movement of the removal tool to an expanded position to uncouple the valve member from the base member.

First actuator tool 180 is disengaged from holding tool 232 at the first location described above, and re-engaged with holding tool 232 such that forked portions 202, 212 capture the outer surface of third and fourth sliding members 246, 248 within annular channels 246b and 248b, as shown in FIG. 13. As indicated above, the location of forked portions 202 and 212 may be reversed with respect to the illustrated embodiment. First and second grips 186, 188 are moved toward each other, thereby moving forked portions 202, 212 away from each other. As a result, third sliding member 246 and fourth sliding member 248 will slide relative to each other such that channels 246b and 248b move away from each other. Movement of third and fourth sliding members 246 and 248 in this manner causes engagement member 340 to move from a collapsed position to an expanded position. As engagement member 340 moves to the expanded position, caps 352 of removal tool 234 move outward, thereby outwardly deflecting or dilating frame 12 of valve member 10, as shown in FIG. 13. Consequently, tab 44 of each mounting portion 42 disengages from lower slot 34 of each coupling element 20, and valve member 10 uncouples from base member 40.

Figure 14:
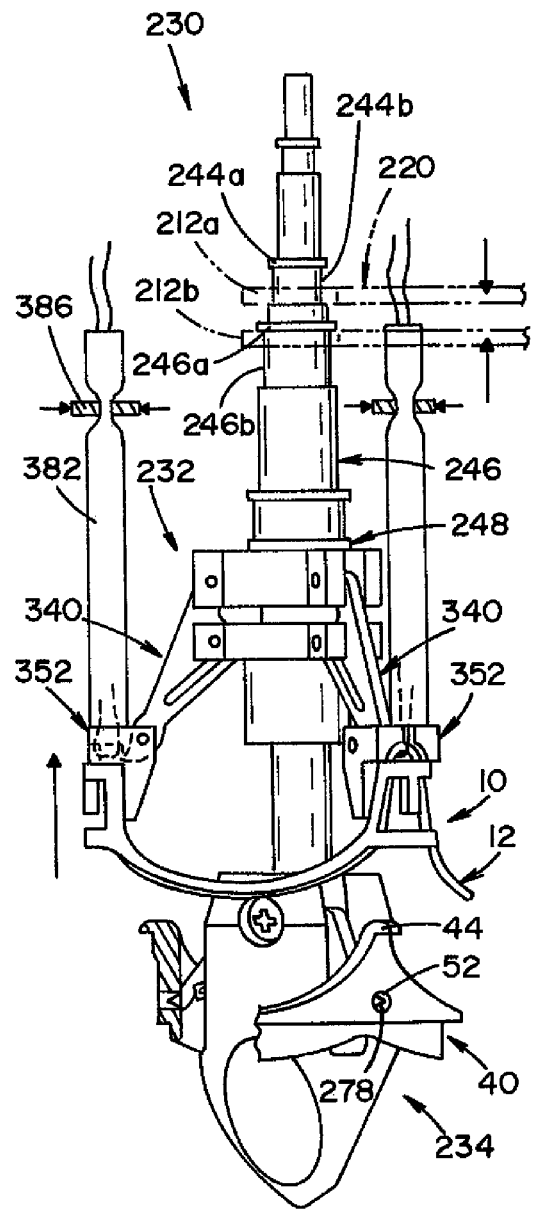
FIG. 14 is an elevational view of the multi-function valve exchange apparatus of FIG. 10, illustrating movement of the removal tool relative to the holding tool to lift and separate the valve member from the base member.

Next, first actuator tool 180 is disengaged from holding tool 232, and second actuator tool 220 is engaged with removal tool 234 such that forked portions 212a, 212b capture the outer surface of second sliding member 244 of holding tool 232 and third sliding member 246 of removal tool 234, within annular channels 244b and 246b (FIG. 14). First and second grips 186, 188 are moved toward each other, thereby moving forked portions 212a, 212b toward each other. As a result, second sliding member 244 and third sliding member 246 will slide relative to each other such that channels 244b and 246b move toward each other. Movement of second and third sliding members 244, 246 in this manner causes removal tool 234 to move relative to holding tool 232, thereby lifting and separating valve member 10 from base member 40, as shown in FIG. 14. The valve removal process is completed by dismounting removal tool 234 from holding tool 232 by generally reversing the steps described above for mounting removal tool 234 onto holding tool 232.

Figure 15:
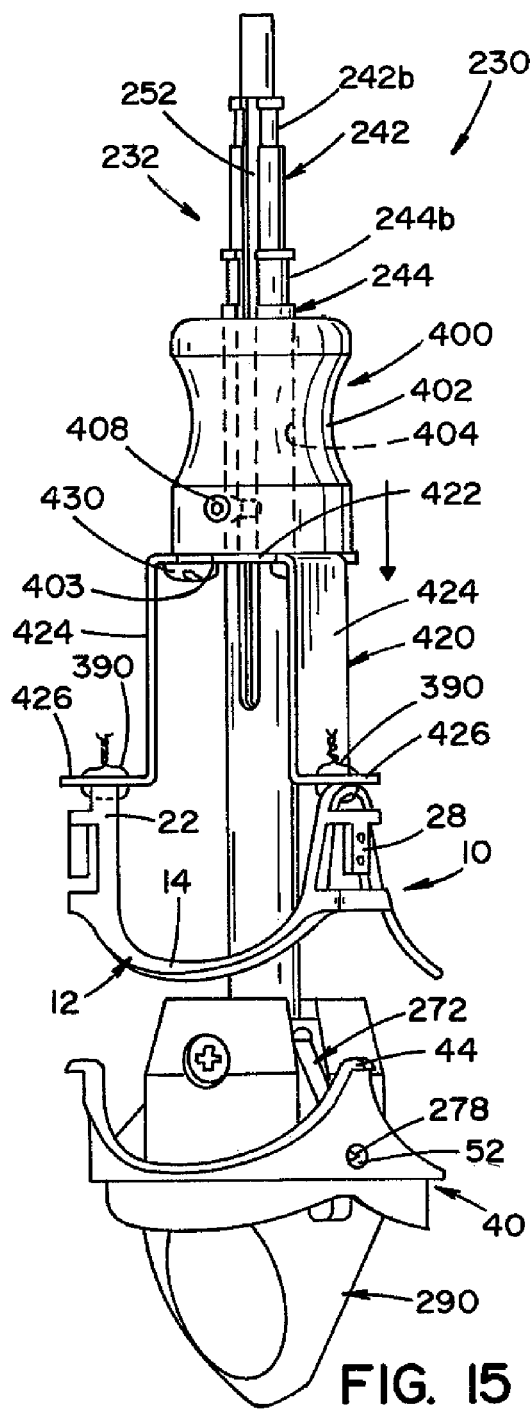
FIG. 15 is an elevational view of the holding tool and an insertion tool of the multi-function valve exchange apparatus, illustrating the insertion tool being guided into position relative to the base member during a process for installing a replacement valve member.

Operation of insertion tool 400 of apparatus 230 to install a new valve member 10 will now be described with particular reference to FIGS. 15-17. Initially, a new valve member 10 is attached to insertion tool 400 by sutures 390. In this regard, a suture 390 is threaded through each upper slot 36 of valve member 10 and the pair of holes 428a, 428b of insertion tool 400. Next, insertion tool 400 is mounted onto holding tool 232. In this regard, insertion tool 400 is positioned such that pin 408 extending through guide sleeve 402 is aligned with elongated slots 252 and 262 of first and second sliding members 242, 244, as best seen in FIG. 18. Guide sleeve 402 slides along elongated slots 252, 262 toward base member 40. Force is applied to insertion tool 400 to couple valve member 10 to base member 40, as shown in FIGS. 16 and 17. After valve member 10 is coupled to base member 40, sutures 390 are cut to separate valve member 10 from insertion tool 400. Thereafter, insertion tool 400 is dismounted from holding tool 232 by generally reversing the steps described above for mounting insertion tool 400 onto holding tool 232.

Next, holding tool 232 is disengaged from base member 40 by generally reversing the steps described above for engaging holding tool 232 with base member 40. In this regard, second actuator tool 220 is engaged with holding tool 232, wherein forked portions 212a, 212b capture the outer surface of first and second sliding members 242, 244 within annular channels 242b and 244b. First and second grips 186, 188 are moved toward each other, thereby moving forked portions 212a, 212b toward each other. As a result, first sliding member 242 and second sliding member 244 will slide relative to each other such that channels 242b and 244b move toward each other. Movement of first and second sliding members 242 and 244 in this manner causes engagement member 270 to move from an expanded position to a collapsed position. Consequently, projections 278 of arms 276 are withdrawn by recesses 52 of base member 40 to disengage holding tool 232 therefrom. Holding tool 232 is then withdrawn from the patient. It will be appreciated that insertion tool 400 may remain mounted to holding tool 232 and removed simultaneously with removal of holding tool 232.

A multi-function valve exchange apparatus 60 according to an alternative embodiment of the present invention will now be described with reference to FIGS. 19-29.

Multi-function valve exchange apparatus 60 includes a stabilizer or holding tool 70, an alignment tool 100 and an extraction or removal tool 130. Removal tool 130 is shown with holding tool 70 in FIGS. 26-29.

Figure 28:
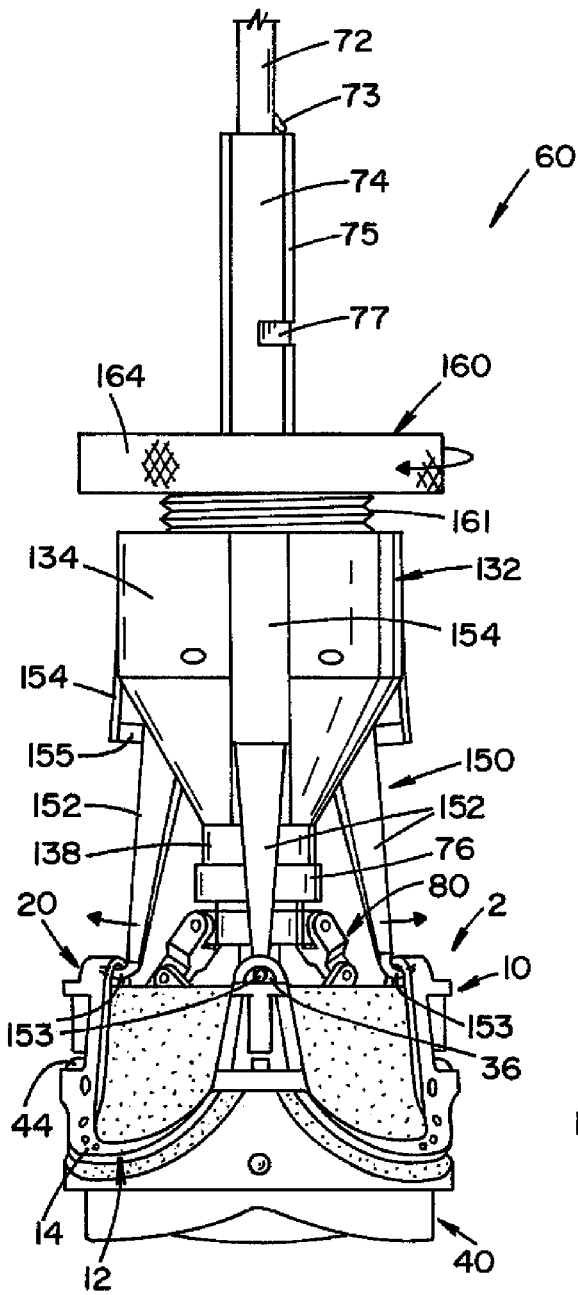
FIG. 28 is an elevational view of the removal tool of FIG. 26 in an expanded position, engaging with the valve member of the valve assembly.

Holding tool 70 will now be described with particular reference to FIGS. 19-25. Holding tool 70 is generally comprised of a first sliding member 72, a second sliding member 74 and an articulating engagement member 80. In the illustrated embodiment, first sliding member 72 takes the form of a cylindrical rod, and second sliding member 74 takes the form of a tubular sleeve. Second sliding member 74 is dimensioned to receive first sliding member 72 such that first sliding member is moveable relative to second sliding member 74. A plurality of ribs 75 extend along the length of the outer surface of second sliding member 74. An annular flange 76 is located at the lower end of second sliding member 74. A removable handle or tab 78 snap-fits onto the outer surface of second sliding member 74. In the illustrated embodiment, a notch 77 is formed in second sliding member 74 to locate tab 78 along the length of second sliding member 74, as best seen in FIG. 28. A spring-biased locking clip 73 (best seen in FIG. 25) is located in first sliding member 72 in order to lock holding tool 70 in an expanded position, as will be described below.

Figure 24:
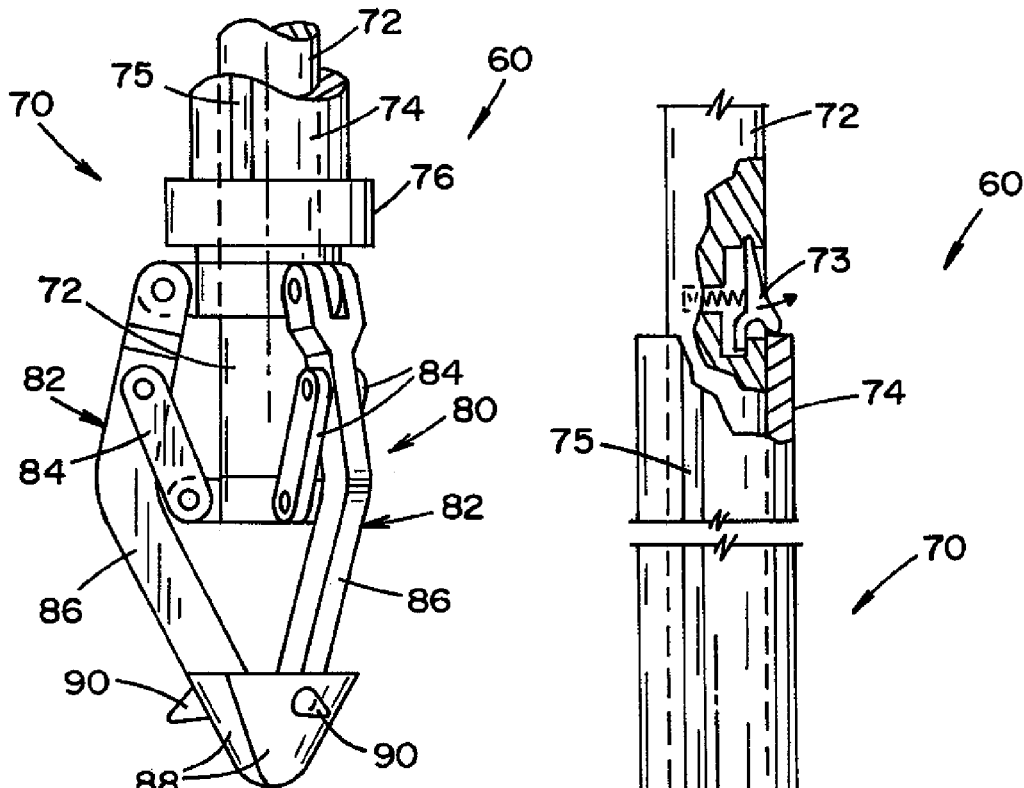
FIG. 24 is an enlarged elevational view of the engagement member of the holding tool shown in FIG. 19, wherein the engagement member is in a collapsed position.
Figure 25:
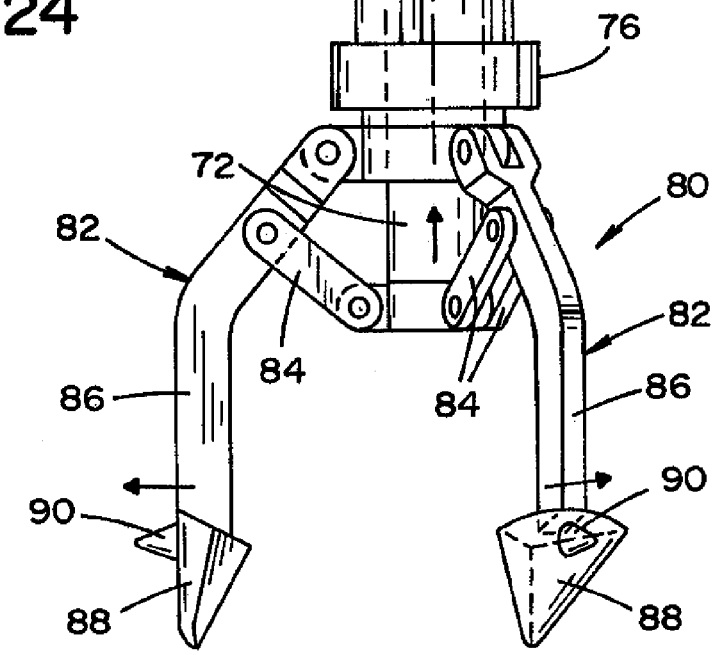
FIG. 25 is an enlarged elevational view of the holding tool shown in FIG. 19, wherein the holding tool is shown locked in a fully expanded position.

One end of first sliding member 72 is connected with second sliding member 74 by articulating engagement member 80, while the other end of first sliding member 72 can be gripped to longitudinally move first sliding member 72 relative to second sliding member 74. Articulating engagement member 80 is comprised of a plurality of articulating joints 82. Each articulating joint 82 includes a link 84 and a leg 86 that are pivotally connected to each other. Link 84 is also pivotally connected at one end with first sliding member 72 and leg 86 is also pivotally connected at one end with second sliding member 74. A triangular wedge 88 having a projection 90 extending outward therefrom is located at the free end of each leg 86, as best seen in FIGS. 24 and 25. Projections 90 are dimensioned to be received by recesses 52 of base member 40, as will be described below. It should be appreciated that projections 90 may have alternative shapes from the illustrated embodiment.

Figure 19:
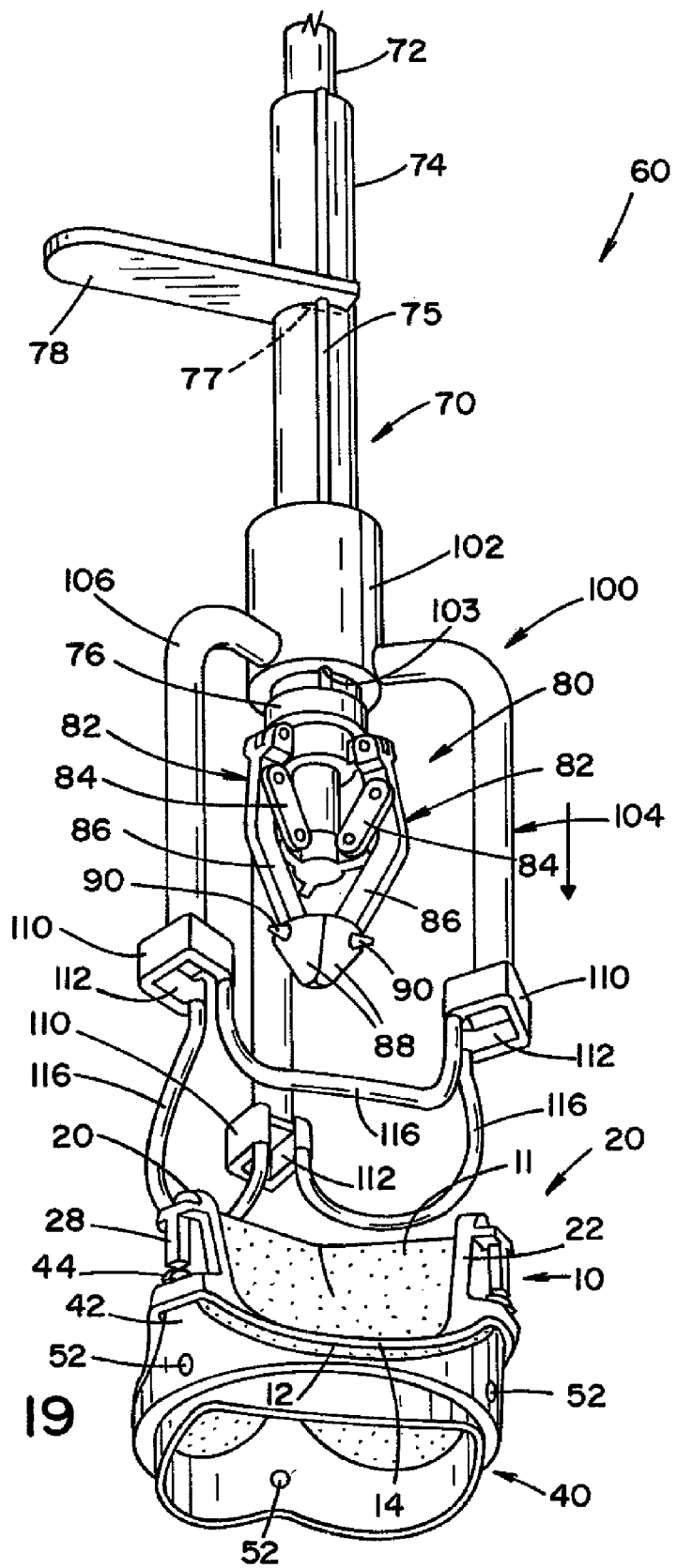
FIG. 19 is a perspective view of an alignment tool and a holding tool of a multi-function valve exchange apparatus according to another embodiment of the present invention, wherein the alignment tool is being guided into position relative to a valve assembly during a process to exchange an installed valve member.
Figure 20:
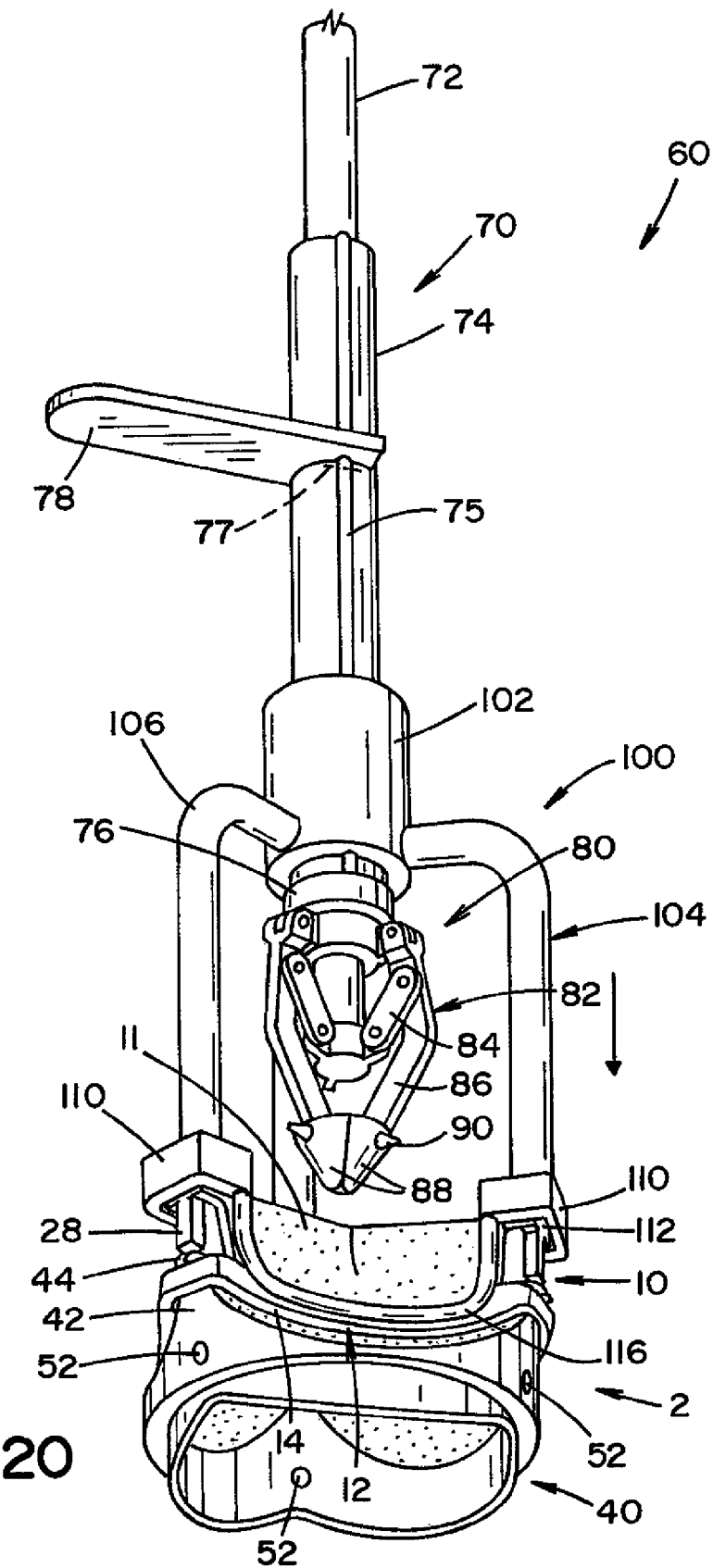
FIG. 20 is a perspective view of the multi-function valve exchange apparatus shown in FIG. 19, illustrating the alignment tool in engagement with the valve assembly.
Figure 21:
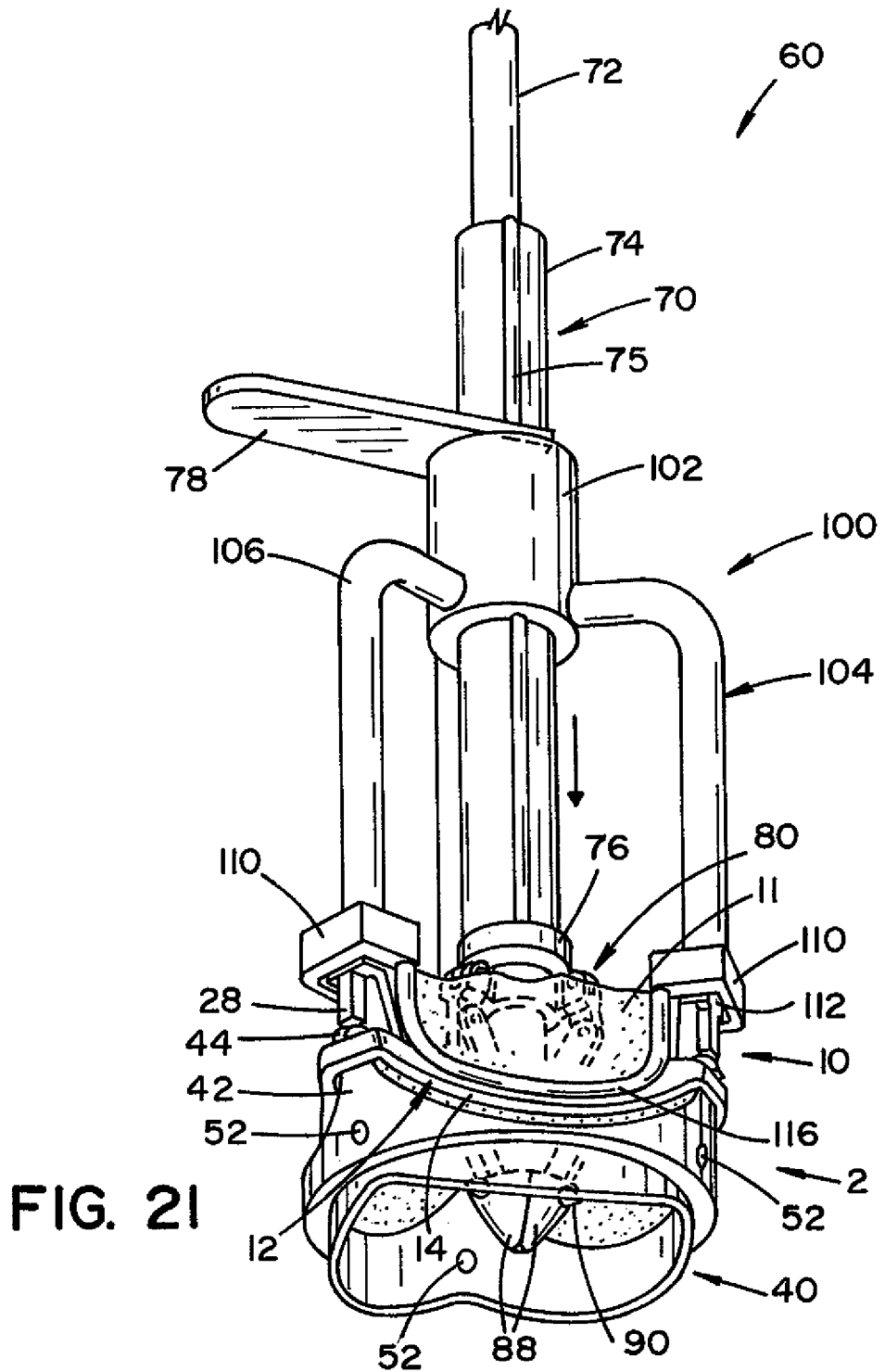
FIG. 21 is a perspective view of the multi-function valve exchange apparatus shown in FIG. 19, illustrating the holding tool being guided into position relative to the base member of the valve assembly.
Figure 22:
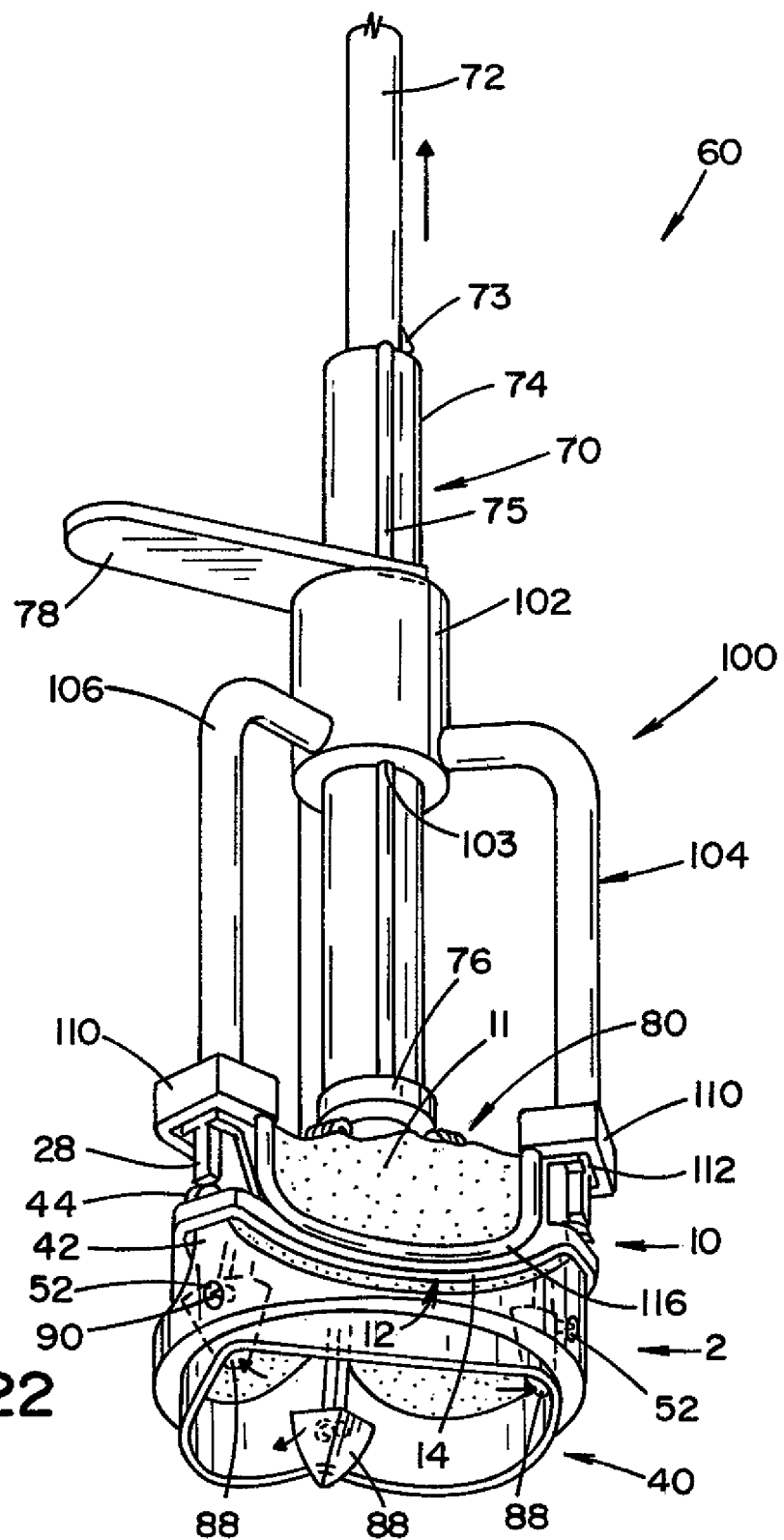
FIG. 22 is a perspective view of the multi-function valve exchange apparatus shown in FIG. 19, illustrating the holding tool in an expanded position in engagement with the base member.
Figure 23:
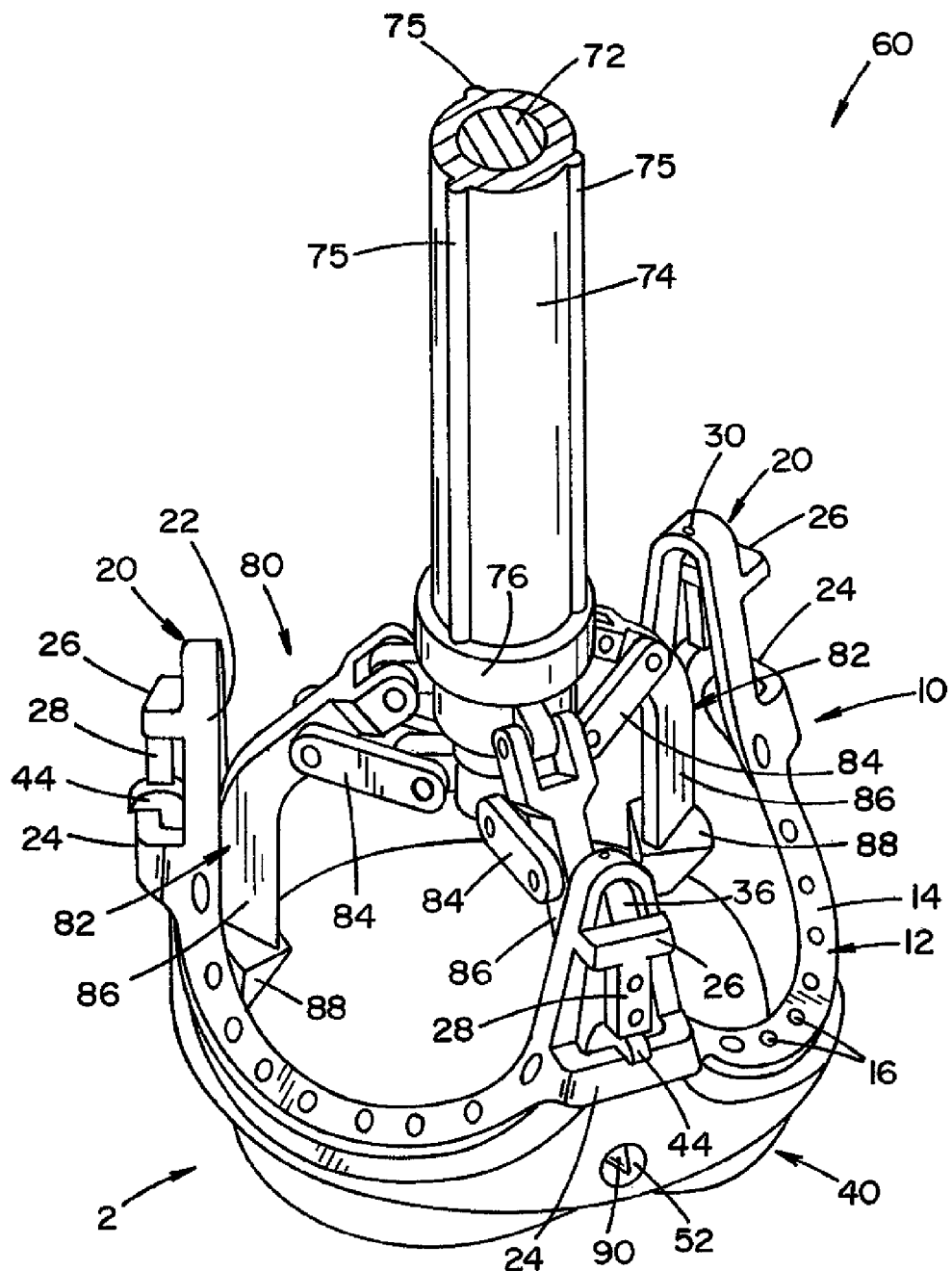
FIG. 23 is an enlarged perspective view of the engagement member of the holding tool of FIG. 22, wherein the engagement member is in an expanded position, engaging with the base member.

As first sliding member 72 is moved relative to second sliding member 74, engagement member 80 moves between a collapsed position (FIGS. 19-21 and 24) and an expanded position (FIGS. 22-23 and 25). As shown in FIGS. 19, 20 and 24, triangular wedges 88 of legs 86 collectively form a conical-shaped tip when engagement member 80 is in the collapsed position. In the expanded position, projections 90 are received by recesses 52 of base member 40 in order to engage holding tool 70 therewith, as best seen in FIG. 23.

Alignment tool 100 will now be described in detail with particular reference to FIGS. 19-22. Alignment tool 100 is generally comprised of a collar portion 102 and an engagement member 104. Collar portion 102 is dimensioned to mount over second sliding member 74 of holding tool 70 In this respect, a plurality of grooves 103 extend along the length of the inner surface of collar portion 102. Grooves 103 are dimensioned to respectively receive ribs 75 of second sliding member 74. Ribs 75 and grooves 103 function to locate holding tool 70 in a proper position relative to valve member 40, such that projections 90 of articulating engagement member 80 are aligned with respective recesses 52 of base member 40 when engagement member 80 is in the expanded position, as shown in FIGS. 22 and 23.

Engagement member 104 is generally comprised of L-shaped arms 106, caps 110 and generally U-shaped connecting members 116. Arms 106 extend outward from collar 102. Caps 110 are located at the distal end of arms 106. Each cap 110 has a recess 112 that is dimensioned to receive a top section of U-shaped portion 22 of coupling elements 20. In the illustrated embodiment, U-shaped connecting members 116 take the form of loops that extend between adjacent caps 110, and are dimensioned to generally match the surface contour of ribbon sections 14 of valve member 10, as seen in FIGS. 20-22.

Valve removal tool 130 will now be described with reference to FIG. 26-29. Removal tool 130 functions to separate and remove valve member 10 from base member 40, and is generally comprised of a body 132, an engagement member 150, and an actuator 160.

Figure 29:
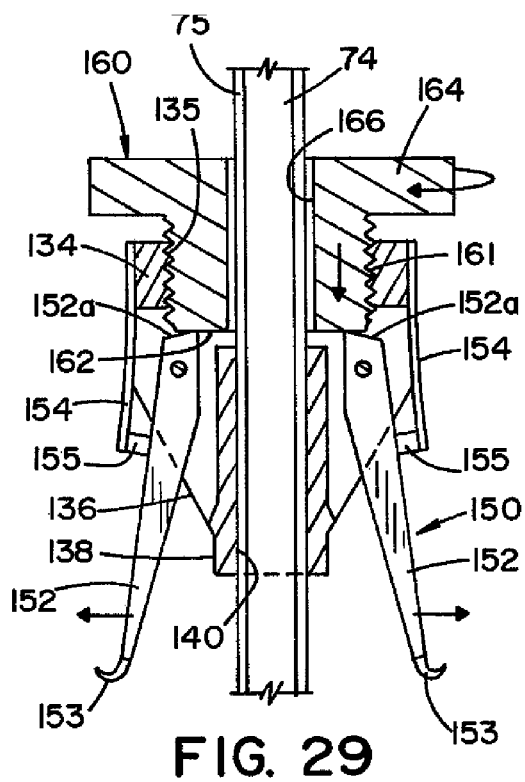
FIG. 29 is a cross-sectional view of the removal tool shown in FIG. 28.

In the illustrated embodiment, body 132 includes a tubular section 134, a conical section 136 and a sleeve 138. Tubular section 134 includes a threaded inner surface 135, as shown in FIG. 29. Sleeve 138 includes an inner channel 139 having grooves 140 formed therein. As can be seen in FIG. 29, the inner and outer diameters of tubular section 134 are respectively larger than the inner and outer diameters of sleeve 138.

Engagement member 150 is generally comprised of a plurality of arms 152 and a plurality of respective bias members 154. A first end of each arm 152 is pivotally mounted to conical section 136 within slots formed therein. Arms 152 include a projection 153 that extends outward therefrom. In the illustrated embodiment, projections 153 take the form of pins or hooks.

Bias members 154 extend downward from the outer surface of tubular section 134, as best seen in FIG. 29. In the illustrated embodiment, bias members 154 are comprised of a metal leaf spring having an inward extending contact element 155 at one end thereof. Bias members 154 bias arms 152 inward toward the outer surface of sleeve 138.

Actuator 160 includes a threaded outer surface 161 and an annular flange 164. Annular flange 164 serves as a gripping element. An inner channel 166 extends through actuator 160. The threads of outer surface 161 are dimensioned to mate with the threads of inner surface 135 of tubular section 134. Furthermore, inner channel 166 of actuator 160 is coaxial with inner channel 139 of sleeve 138. As actuator 160 is rotated and threaded deeper into tubular section 134, front face 162 of actuator 160 engages tapered surfaces 152a of arms 152, thereby causing arms 152 to pivot outward against the biasing force of bias members 154 (FIG. 29). Accordingly, projections 153 of arms 152 extend outward, away from the outer surface of sleeve 138.

A method for exchanging valve member 10 of an installed valve assembly 2, and the detailed operation of multi-function valve exchange apparatus 60, comprised of holding tool 70, alignment tool 100 and removal tool 130, will now be described with particular reference to FIGS. 19-29.

Initially, alignment tool 100 mounted onto holding tool 70. In this regard, collar portion 102 is position such that grooves 103 are aligned with ribs 75 of second sliding member 74. Alignment tool 100 is then located relative to valve assembly 2 such that connecting members 116 are located adjacent to respective ribbon sections 14 of valve member 10, thereby contacting leaflets 11 mounted to valve member 10 (FIGS. 19 and 20). As a result, caps 110 of alignment tool 100 are coarsely aligned with respective coupling elements 20 of valve member 10. Additional positioning of alignment tool 100 relative to valve assembly 2 is carried out by seating each cap 110 onto a respective U-shaped portion 22 of coupling elements 20 (FIG. 29).

Next, holding tool 70 is advanced toward valve assembly 2 by moving second sliding member 74 relative to collar portion 102 of alignment tool 100, such that tab 78 abuts the top face of collar portion 102, as shown in FIG. 21. Engagement member 80 is now properly positioned for engagement with base member 40.

Once engagement member 80 is properly positioned relative to base member 40, engagement member 80 is moved from the collapsed position (FIGS. 20, 21 and 24) to the expanded position (FIGS. 22, 23 and 25). In this respect, holding tool 70 is moved from the collapsed position to the expanded position by sliding first sliding member 72 relative to second sliding member 74 such that spring-biased locking clip 73 clears the top face of second sliding member 74 and springs outward, as best seen in FIG. 25. As first sliding member 72 is moved relative to second sliding member 74, legs 86 of engagement member 80 expand outward, as shown in FIG. 25. When engagement member 80 is fully expanded, projections 90 of legs 86 will be respectively received into recesses 52 of base member 40, as best seen in FIG. 23. Locking clip 73 locks engagement member 80 in the expanded position.

Next, alignment tool 100 is dismounted from holding tool 70 by generally reversing the steps described above for mounting alignment tool 100 onto holding tool 70. In this regard, tab 78 is removed from notch 77 of second sliding member 74, and collar portion 102 is moved relative to second sliding member 74 such that alignment tool 100 moves away from valve assembly 2.

Next, removal tool 130 is mounted to holding tool 70 by aligning grooves 140 of sleeve 138 with ribs 75 of second sliding member 74, as best seen in FIG. 27. Accordingly, removal tool 130 is pre-aligned with coupling elements 20 of valve member 10. Removal tool 130 is moved relative to second sliding member 74 (FIG. 26) such that the front face of sleeve 138 abuts flange 76 of second sliding member 74 (FIG. 28). At this position, projections 153 of arms 152 are properly aligned relative to upper slots 36 of coupling elements 20.

Actuator 160 of removal tool 130 is then rotated to outwardly expand arms 152, as illustrated in FIG. 28. Annular flange 164 provides a gripping surface to facilitate rotation of actuator 160. As arms 152 expand outward, projections 152 extend through respective upper slots 36 of coupling elements 20. Additional rotation of actuator 160 causes arms 152 to engage with coupling elements 20, and outwardly deflect and dilate frame 12 such that lower slots 34 of coupling elements 20 are clear of tabs 44 of base member 40. Accordingly, the outward expansion of arms 152 uncouples valve member 10 from base member 40.

Removal tool 130 continues to engage and hold valve member 10, and is dismounted from holding tool 70 by generally reversing the steps described above for mounting removal tool 130 onto holding tool 70. In this regard, removal tool 130 is moved relative to second sliding member 74 such that removal tool 130 moves away base member 40, thereby completing removal of valve member 10.

A new replacement valve member 10 may be installed using a tool similar to the above-described valve insertion tool 400, or a tool that functions similar to the above-described removal tool 130.

It should be understood that the components of the multiple embodiments described above may be modified and combined in ways not illustrated herein to form alternative configurations consistent with the present invention. For example, the foregoing valve exchange procedures have been described in connection with an "open chest" approach. It is contemplated that the methods and apparatus of the present invention are suitably adaptable for use in connection with a transapical approach. Furthermore, the location of projections/protuberances of the above-described tools and the mating recesses/slots of the valve assembly may be reversed, such that the projections/protuberances are located on the valve assembly and the mating recesses/slots are located on the tools.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention.

Having described the invention, the following is claimed:

1. A multi-function valve exchange apparatus for facilitating exchange of a valve member of a valve assembly that includes a valve member detachably coupled to a base member, the apparatus comprising: a holding tool including:
a first engagement member moveable between a collapsed position and an expanded position, wherein said first engagement member is configured to grip the base member in the expanded position; and first and second sliding members moveable relative to each other to move the first engagement member between the collapsed and expanded positions; and
a removal tool detachably mountable to said holding tool and moveable relative thereto, said removal tool including: a second engagement member moveable between a collapsed position and an expanded position, wherein said second engagement member is configured to grip the valve member of said valve assembly in the expanded position to uncouple said valve member from said base member.

2. The multi-function valve exchange apparatus according to claim 1, wherein said removal tool further comprises:
first and second sliding members moveable relative to each other to move said second engagement member between the collapsed and expanded positions.

3. The multi-function valve exchange apparatus according to claim 1, wherein said second engagement member includes a plurality of arms, each arm pivotally mounted to one of said first and second sliding members.

4. The multi-function valve exchange apparatus according to claim 3, wherein each said arm has a projection dimensioned to be received by an opening in said valve member.

5. The multi-function valve exchange apparatus according to claim 4, wherein a cap is pivotally mounted to each of said arms, said cap engageable with the valve member of the valve assembly.

6. The multi-function valve exchange apparatus according to claim 1, wherein said removal tool further comprises: a rotatable actuator for moving said second engagement member between the collapsed and expanded positions.

7. The multi-function valve exchange apparatus for facilitating exchange of a valve member of a valve assembly that includes a valve member detachably coupled to a base member, the apparatus comprising:
a holding tool including:
a first engagement member moveable between a collapsed position and an expanded position, wherein said first engagement member is configured to grip the base member in the expanded position; and first and second sliding members moveable relative to each other to move the first engagement member between the collapsed and expanded positions; and
an insertion tool detachably mountable to said holding tool and moveable relative thereto, wherein said insertion tool includes: a guide sleeve for guiding movement of the insertion tool relative to said holding tool; and a second engagement member attached to the guide sleeve, wherein a new valve member is attachable to the second engagement member.

8. The multi-function valve exchange apparatus according to claim 7, wherein said new valve member is attached to said second engagement member by sutures.

9. A multi-function valve exchange apparatus for facilitating exchange of a valve member of a valve assembly that includes a valve member detachably coupled to a base member, the apparatus comprising:
a holding tool including:
a first engagement member moveable between a collapsed position and an expanded position, wherein said first engagement member is configured to grip the base member in the expanded position; and first and second sliding members moveable relative to each other to move the first engagement member between the collapsed and expanded positions; and an alignment tool detachably mountable to the holding tool and moveable relative thereto, wherein said alignment tool includes:
a collar portion; and
a second engagement member comprising:
a plurality of arms extending from the collar portion; and
a plurality of caps for engagement with said valve member of said valve assembly, wherein each cap is connected with one of said arms.

10. The multi-function valve exchange apparatus according to claim 9, wherein said second engagement member further comprises:
a plurality of U-shaped connecting members extending between adjacent caps, wherein each said U-shaped connecting member generally matches a surface contour of a ribbon section of said valve member.

11. A multi-function valve exchange apparatus for facilitating exchange of a valve member of a valve assembly that includes a valve member detachably coupled to a base member, the apparatus comprising:
a holding tool including:
a first engagement member moveable between a collapsed position and an expanded position, wherein said first engagement member is configured to grip the base member in the expanded position; and
first and second sliding members moveable relative to each other to move the first engagement member between the collapsed and expanded positions; and
a removal tool detachably mountable to said holding tool and moveable relative thereto, said removal tool including:
a second engagement member moveable between a collapsed position and an expanded position, wherein said second engagement member is configured to grip the valve member of said valve assembly in the expanded position to uncouple said valve member from said base member; and
an insertion tool detachably mountable to said holding tool and moveable relative thereto, wherein said insertion tool includes:
a guide sleeve for guiding movement of the insertion tool relative to said holding tool; and
a third engagement member attached to the guide sleeve, wherein a new valve member is attachable to the third engagement member.

12. The multi-function valve exchange apparatus according to claim 11, wherein said multi-function valve exchange apparatus further comprises:
an alignment tool detachably mountable to the holding tool and moveable relative thereto, wherein said alignment tool includes:
a collar portion; and
a fourth engagement member comprising:
a plurality of arms extending from the collar portion; and
a plurality of caps for engagement with said valve member of said valve assembly, wherein each cap is connected with one of said arms.

* * * * *